US006667038B1

(12) United States Patent
Donta et al.

(10) Patent No.: US 6,667,038 B1
(45) Date of Patent: Dec. 23, 2003

(54) PREVENTION, DIAGNOSIS AND TREATMENT OF LYME DISEASE

(75) Inventors: Sam T. Donta, Boston, MA (US); Mark J. Cartwright, West Newton, MA (US)

(73) Assignee: Boston Medical Center Corp., Boston, MA (US)

( * ) Notice: Subject to any disclaimer, the term of this patent is extended or adjusted under 35 U.S.C. 154(b) by 0 days.

(21) Appl. No.: 09/553,863

(22) Filed: Apr. 20, 2000

Related U.S. Application Data

(60) Provisional application No. 60/130,380, filed on Apr. 21, 1999.

(51) Int. Cl.[7] ........................ A61K 39/02; A61K 39/38

(52) U.S. Cl. ................. 424/190.1; 424/9.2; 424/184.1; 424/234.1; 424/236.1; 424/262.1; 530/300; 530/350; 536/23.1; 536/23.7

(58) Field of Search .............................. 424/9.2, 184.1, 424/185.1, 234.1, 236.1, 262.1, 190.1; 530/300, 350; 536/23.1, 23.7

(56) References Cited

U.S. PATENT DOCUMENTS 5,530,103 A * 6/1996 Livey et al. ................ 530/416

OTHER PUBLICATIONS

Fraser, et al, "Genomic Sequence of a Lyme Disease Spirochaete . . . " Accession No. B70194, 1997.*

* cited by examiner

*Primary Examiner*—Rodney P Swartz
(74) *Attorney, Agent, or Firm*—Brinks Hofer Gilson & Lione

(57) ABSTRACT

The present invention provides compositions and methods related to *Borrelia burgdorferi* toxin and antitoxin preparations. In particular, the present invention provides methods and compositions for the diagnosis of Lyme disease, as well as for use in treating subjects infected with *B. burgdorferi* through passive immunization, and vaccine development.

27 Claims, 4 Drawing Sheets

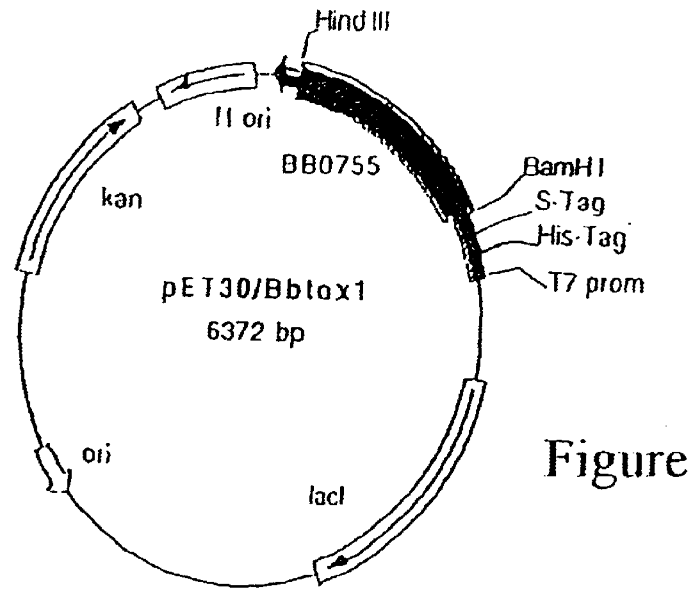
Figure 2
Figure 3
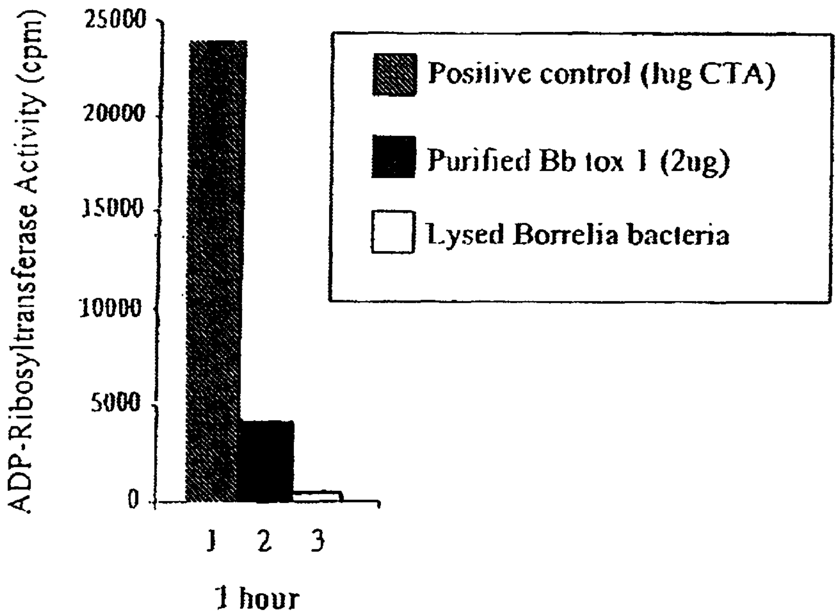

PREVENTION, DIAGNOSIS AND TREATMENT OF LYME DISEASE

RELATED APPLICATIONS

This application claims priority under 35 U.S.C. §119(e) from Provisional U.S. patent Application Ser. No. 60/130,380 filed Apr. 21, 1999, entitled PREVENTION, DIAGNOSIS AND TREATMENT OF LYME DISEASE. The contents of the provisional application are hereby expressly incorporated by reference.

FIELD OF THE INVENTION

The present invention provides compositions and method related to *Borrelia burgdorferi* toxins, in particular, the present invention provides methods and compositions for the diagnosis, treatment and prevention of Lyme disease.

BACKGROUND OF THE INVENTION

Lyme disease is a potentially severe and complex multisystem disorder associated with the tick-borne spirochete *Borrelia burgdorferi*. The disease is transmitted to humans and other animals through arthropod bites. Indeed, with few exceptions (e.g., *B. recurrentis* and *B. duttonii*), all Borrelia species are maintained in nature by cycling through the wild animals (e.g., deer, rodents and fowl) and the ticks that feed upon them. Lyme disease was first officially recognized in North America in 1975, and has become recognized as the most prevalent tick-borne disease in the U.S. This recognition was due to an outbreak of disease in children in Lyme, Conn. The disease is now recognized as having a worldwide distribution, with cases recorded in may countries around the world. Lyme disease seems to be more severe than erythema chronicum migrans, a tick-borne syndrome reported in Europe, as early as 1908. The etiologic agent, *B. burgdorferi* remained unidentified until 1981, when it was isolated from *Ixodes scapularis* (*I. dammini*) from New York and later in the European tick vector *I. ricinus* (See, Schwan, et al., "Borrelia" in Murray, et al., [eds]. *Manual of Clinical Microbiology*, 6th ed., ASM Press, Washington, D.C., 1995, pp. 625–635). In addition to infection acquired through tick bites, infected tissues of mammalian reservoirs or patients may also transmit disease.

In the northeastern United States, Wisconsin and Minnesota, the deer tick, *Ixodes dammini* is the primary vector, while in the western United States and Europe, *I. pacifious* and *I. ricinus* are the main vectors, respectively. It is also possible that ticks of other genera may transmit the disease (See, Schwan, et al., "Borrelia" in Murray, et al., [eds]. *Manual of Clinical Microbiology*, 6th ed., ASM Press, Washington, D.C., 1995, pp. 625–635). The prevalence of infected ticks appears to vary widely among geographic regions, and is directly proportional to the reported number of lyme disease cases in a given location (See, e.g., Persing, et al., *J. Clin. Microbiol*., 1990, 28, 566–572).

Although there is not universal agreement, it appears that the Lyme disease spirochete, *B. burgdoferi* sensu lato, may be divided into three separate species, *B. burdorferi* sensu stricto, *B. garinii*, and *B. afzelii*. There appears to be no vector specificity among these proposed species, nor it is clear as to whether they cause identical diseases. However, preliminary studies conducted in Europe have indicated that different clinical manifestations may be associated with these three species (See, Schwan, et al., "Borrelia" in Murray, et al., [eds]. *Manual of Clinical Microbiology*, 6th ed., ASM Press, Washington, D.C., 1995, pp. 625–635).

The clinical symptoms of Lyme disease vary among individuals and during the time course of infection, and range from a relatively benign skin rash to severe arthritic, neurologic and cardiac manifestations. The most common clinical manifestation is the distinctive skin rash ("erythema migrans," "erythema chronicam migrans," or "ECM") which follows the bite of an infected tick. This rash is often accompanied by headache, stiff neck, myalgias, arthralgias, malaise, fatigue, and/or lymph node swelling. Weeks to months later, some infected patients develop meningoencephalitis, myocarditis, or migrating musculoskeletal pain. Even later in the course of disease, patients may experience intermittent attacks of oligoarticular arthritis or chronic arthritis in large joints, particularly in the knee. While Lyme disease appears to progress to dermatologic and neurologic manifestations more frequently in Europe, arthritis is a more common late manifestation observed in U.S. patients (See, Rose, et al., *J. Clin. Microbiol*., 1991, 29:524–432). Other clinical syndromes reported in Europe that may have the same etiologic agent include lymphocytoma (lymphadenosis benigna cutis), acrodermalitis chronica atrophicans, tick-borne meningoradiculitis (Garin-Bujadoux-Bannwarth's syndrome), and myositis. Due to increased awareness and reporting, reported cases of Lyme disease have increased over time. Between 1982 and 1992, approximately 50,000 cases of Lyme disease were reported to the Centers for Disease Control (CDC), with 48 states reporting cases by 1992.

Treatment of Lyme disease typically consisting of oral antimicrobial therapy at the initial stages and high dosage intravenous antimicrobial therapy for the later manifestations. While treatment is often successful, symptoms sometimes persist or reappear after treatment, particularly during the later stages of disease (See, e.g., Rose and Schwan, *J. Infect. Dis*., 1989, 160:1018–1029). Chronic Lyme disease is difficult to treat with current antimicrobial regimes (Donta, et al., *Clin. Infect. Dis*., 1997, 25:552–555).

With the dramatic increase in public awareness of the disease, its prevalence and geographical distribution of Lyme borreliosis, a tremendous new demand has been placed on laboratories to confirm cases using methods such as serology (See, Simpson, et al., *J. Clin. Microbiol*., 1990, 28:1329–1337). However, diagnosis of Lyme disease is often not straightforward. For example, there are well-documented Lyme disease cases for which knowledge of tick bite, skin rash, or positive serology are lacking. Most of the systemic manifestations of advanced Lyme disease are not unique to the disease and observation of spirochetes in patients is difficult (See, Rosa and Schwan, *J. Infect. Dis*., 1989, 160:1018–1029; Rosa, et al., *J. Clin. Microbiol*., 1991, 29:524–532). In addition, strong, specific immunologic responses are not always observed.

Furthermore, many problems have been reported with currently available serological tests, including both false positives and false negatives. Some tests have focused on the flagellar protein of *B. burgdorferi* as a means to increase the sensitivity of the serological tests because early studies indicate that the 41 kD flagellar subunit (flagellin) generated the earliest immune response in infected humans (See, e.g., Simpson, et al., *J. Clin. Microbiol*., 1990, 28:1329–1337 for a brief review). However, potential factors have been considered problematic with the use of flagellar protein, including the cross-reactivity of antibodies to flagella of other Borrelia species, as well as other organisms such as *Treponema pallidum*. This has led others to investigate the use of a 39 kDa non-flagellar *B. burgdoferi* antigen that is immunoreactive with many sera from human Lyme disease patients (See, Simpson, et al., *J. Clin. Microbiol*., supra).

Additional factors complicate the serologic diagnosis of Lyme disease. For example, serology is often less useful during the early stages of disease (i.e., during primary Lyme disease), as many patients with ECM have not formed sufficient antibody levels to be detectable in many assays (See, e.g., Coleman and Benach, *J. Infect. Dis*., 1987, 155:756–765). Antigen detection in urine, blood, and other tissues by a dot blot immunoassay and an antigen capacity assay using colloidal gold-immune electron microscopy have also been tried. However, these antigen detection methods are apparently no longer available (See, Schwan, et al., "Borrelia," in Murray, et al., [eds], *Manual of Clinical Microbiology*, 6th ed., ASM Press, Washington, D.C., 1995, pp.626–635).

In sum, much remains to be learned regarding Lyme disease and the pathogenic mechanisms associated with the disease. In addition, much remains to be learned regarding the organisms themselves. One complicated factor is the difficulty of culturing the organisms in the laboratory. Indeed, the maintenance of infectious spirochetes, requires the use of laboratory animals (e.g., rats, mice, or live colonies of infected ticks). Nonetheless, some investigations have provided useful information regarding the organism.

At lest one strain of *B. burgdorferi* (B31) has been reported to harbor a single linear chromosome of approximately one megabase pairs in size, making it one of the smallest bacterial genomes known (See, Casjens and Huang, *Mol. Microbiol*., 1993, 8:967–980). This chromosomal structure is a striking feature of these organisms, as no other bacterial groups are known to have linear chromosomes (Casjens and Huang, supra). These organisms are also somewhat unique among bacteria in that they carry numerous linear DNA molecules with covalently closed ends ("linear plasmids") (Simpson, et al., *Infect. Immun*., supra). The major outer membrane proteins "OspA" and "OspB" are encoded by a 49 kilobase pair (kb) linear plasmid in *B. burgdorferi* B31, and are carried on similarly-sized plasmids in other isolates.

Although the functions of OspA and OspB remains to be elucidated, it is possible that OspB plays a role in adherence. Although antibodies to these antigens have also been detected in the sera of Lyme disease patients, their use as serodiagnostic agents can be questioned due to their lack of antigenic stability.

A recombinant OspA vaccine, with a reported 70–80% preventative efficacy has been recently developed (See, Steere, et al., *New Engl. J. Med*, 1998, 339:209–215; Meurice, et al, *Clin. Infect. Dis*., 1997, 25 Suppl. 1:S71–75; and Parenti, et al, "The Safety and Efficacy of an Adjuvanted Lyme Disease Vaccine," in 11th *International Scientific Conference on Lyme Disease and Other Spirochetal and Tick-Borne Disorders*, 1998, New York), but it is uncertain whether it will prevent the establishment of infection and long-term sequelae. Indeed, it is possible that this vaccine will prove to be harmful to patients who have previously contracted Lyme disease.

Syphilis is a chronic systemic infection caused by *Treponema pallidum*, and is characterized by a primary lesion that appears following an incubation period of ~3 weeks, and is usually associated with regional lymphadenopathy. A secondary bacteremic stage is associated with generalized mucocutaneous lesions and generalized lymphadenopathy, followed by a latent period of subclinical infection lasting many years. In about one third of untreated cases, the tertiary stage is characterized by progressive destructive mucocutaneous, musculoskeletal or parenchymal lesions, aortitis, or symptomatic central nervous disease.

In view of debilitating nature of the advanced stages of the disease, compositions and methods for accurate diagnosis, as well as methods and compositions for treatment and disease prevention remain critical. However, these needs have not previously been satisfactorily met.

SUMMARY OF THE INVENTION

The present invention provides compositions and methods related to *Borrelia burgdorferi* and *Treponema pallidum* toxins. In particular, the present invention provides methods and compositions for the diagnosis, treatment and prevention of Lyme disease (*Borrelia burgdorferi*) and Syphilis (*Treponema pallidum*).

The invention provides isolated nucleic acid molecules, unique fragments of those molecules, expression vectors containing the foregoing, and host cells transfected with those molecules. The invention also provides isolated binding polypeptides and binding agents which bind such polypeptides, including antibodies. The foregoing can be used, inter alia, in the diagnosis or treatment of conditions characterized by the expression of a *Borrelia burgdorferi* toxin, Bbtox1, and by the expression of a *Treponema pallidum* toxin, Tptox1, nucleic acid or polypeptide.

According to one aspect of the invention, isolated nucleic acid molecules that code for a Bbtox1 and/or a Tptox1 polypeptide are provided and include: (a) nucleic acid molecules which hybridize under stringent conditions to a molecule selected from the group consisting of a nucleic acid of SEQ ID NO:1, SEQ ID NO:3 and/or SEQ ID NO:17, and which code for a Bbtox1 (SEQ ID NO:1, SEQ ID NO:3) and/or a Tptox1 (SEQ ID NO:17) polypeptide, (b) deletions, additions and substitutions of (a) which code for a respective Bbtox1 and/or Tptox 1 polypeptide, (c) nucleic acid molecules that differ from the nucleic acid molecules of (a) or (b) in codon sequence due to the degeneracy of the genetic code, or (d) full-length complements of (a), (b) or (c). In certain embodiments, the isolated nucleic acid molecule comprises nucleotides 1–957 of SEQ ID NO:1. In some embodiments the isolated nucleic acid molecules are those comprising nucleotides 1–957 of SEQ ID NO:3. In further embodiments, the isolated nucleic acid molecule comprises nucleotides 1–762 of SEQ ID NO:17. The isolated nucleic acid molecule also can comprise a molecule which encodes the polypeptide of SEQ ID NO:2 or the polypeptide of SEQ ID NO:4, and has Bbtox1 toxin activity. The isolated nucleic acid molecule can further comprise a molecule which encodes the polypeptide of SEQ ID NO:18 and has Tptox1 toxin activity.

The invention in another aspect provides an isolated nucleic acid molecule selected from the group consisting of (a) a unique fragment of nucleic acid molecule of SEQ ID NO:1, SEQ ID NO:3, and/or SEQ ID NO:17 (of sufficient length to represent a sequence unique within the human genome), (b) full-length complements of (a), provided that the fragment includes a sequence of contiguous nucleotides which is not identical to a sequence selected from the sequence group consisting of (1) sequences having the GenBank accession numbers of Table 1, (2) full-length complements of (1), and (3) fragments of (1) and (2).

In one embodiment, the sequence of contiguous nucleotides is selected from the group consisting of (1) at least two contiguous nucleotides nonidentical to the sequence group, (2) at least three contiguous nucleotides nonidentical to the sequence group, (3) at least four contiguous nucleotides nonidentical to the sequence group, (4) at least five contiguous nucleotides nonidentical to the sequence group, (5) at least six contiguous nucleotides nonidentical to the sequence group, (6) at least seven contiguous nucleotides nonidentical to the sequence group.

In another embodiment, the fragment has a size selected from the group consisting of at least: 8 nucleotides, 10 nucleotides, 12 nucleotides, 14 nucleotides, 16 nucleotides, 18 nucleotides, 20, nucleotides, 22 nucleotides, 24 nucleotides, 26 nucleotides, 28 nucleotides, 30 nucleotides, 40 nucleotides, 50 nucleotides, 75 nucleotides, 100 nucleotides, 200 nucleotides, 1000 nucleotides and every integer length therebetween.

According to another aspect, the invention provides expression vectors, and host cells transformed or transfected with such expression vectors, comprising the nucleic acid molecules described above.

According to another aspect of the invention, an isolated polypeptide is provided. The isolated polypeptide is encoded by the foregoing isolated nucleic acid molecules of the invention. In some embodiments, the isolated polypeptide is encoded by the nucleic acid of SEQ ID NO:1, giving rise to a polypeptide having the sequence of SEQ ID NO:2 that has Bbtox1 toxin activity. In certain embodiments, the isolated polypeptide is encoded by the nucleic acid of SEQ ID NO:3, giving rise to a polypeptide having the sequence of SEQ ID NO:4 that has Bbtox1 toxin activity. In further embodiments, the isolated polypeptide is encoded by the nucleic acid of SEQ ID NO:17, giving rise to a polypeptide having the sequence of SEQ ID NO:18 that has Tptox1 toxin activity. In other embodiments, the isolated polypeptide may be a fragment or variant of the foregoing of sufficient length to represent a sequence unique within the human genome, and identifying with a polypeptide that has Bbtox1 and/or Tptox1 toxin activity. In another embodiment, immunogenic fragments of the polypeptide molecules described above are provided.

According to another aspect of the invention, isolated binding polypeptides are provided which selectively bind a polypeptide and/or at least one antigen determinate on a polypeptide encoded by the foregoing isolated nucleic acid molecules of the invention. Preferably the isolated binding polypeptides selectively bind a polypeptide (and/or at least one antigen determinate on a polypeptide) which comprises the sequence of SEQ ID NO:2, SEQ ID NO:4, or fragments thereof, and that do not recognize ("cross-react") with epitopes from toxin polypeptides of *V. cholerae, E. coli, B. perfussis, P. aeruginosa, T pallidum*, and/or *C. diptheriae*. Additionally, the isolated binding polypeptides, preferably, selectively bind a polypeptide (and/or at least one antigen determinate on a polypeptide) which comprises the sequence of SEQ ID NO:18, or fragments thereof, and that do not recognize ("cross-react") with epitopes from toxin polypeptides of *V. cholerae, E. coli, B. pertussis, P. aeruginosa, B. burgdorferi*, and/or *C. diptheriae*. In preferred embodiments, the isolated binding polypeptides include antibodies and fragments of antibodies (e.g., Fab, $F(ab)_2$, Fd and antibody fragments which include a CDR3 region which binds selectively to the Bbtox1 polypeptide). The present invention encompasses polyclonal, as well as monoclonal antibodies.

The invention also contemplates kits comprising a package including assays for Bbtox1 epitopes, Bbtox1 nucleic acids, and/or Tptox1 epitopes, Tptox1 nucleic acids,and instructions, and optionally related materials such as controls, for example, a number, color chart, or an epitope of the expression product of the foregoing isolated nucleic acid molecules of the invention, for comparing the level of Bbtox1 and/or Tptox1 polypeptides, or Bbtox1 and/or Tptox1 nucleic acid forms in a test sample to the level in a control sample. This comparison can be used to assess in a subject a risk of developing Lyme disease (Bbtox1) and or Syphilis (Tptox1). The kits may also include assays for other known genes, and expression products thereof, associated with other infectious agents.

The present invention also provides a fusion protein(s) comprising a portion of Bbtox1 protein and a non-toxin protein sequence. In particularly preferred embodiments, the Bbtox1 protein comprises the sequence of SEQ ID NO:2 or SEQ ID NO:4.

The present invention also provides a fusion protein(s) comprising a portion of Tptox1 protein and a non-toxin protein sequence. In particularly preferred embodiments, the Tptox1 protein comprises the sequence of SEQ ID NO:18.

According to another aspect of the invention, a method for determining the level of Bbtox1 expression in a sample is provided. The method involves measuring expression of Bbtox1 in a test sample, and comparing the measured expression of Bbtox1 in the test sample to a control, as a measure of the level of Bbtox1 expression. The control can be a negative control, or a quantitated control of Bbtox1 expression. In one embodiment, the test sample is obtained from a subject suspected of being infected with *B. burgdorferi*. In certain embodiments, the test sample is a *B. burgdorferi* culture or isolate. Expression of Bbtox1 in the test sample can be Bbtox1 mRNA expression and/or Bbtox1 polypeptide expression. In some embodiments, Bbtox1 mRNA expression can be measured using the Polymerase Chain Reaction and/or northern blotting. In certain embodiments, Bbtox1 polypeptide expression can be measured using monoclonal and/or polyclonal antisera to Bbtox1. In further embodiments, the test sample can be tissue or a biological fluid.

The present invention also provides methods for producing anti-Bbtox1 antibodies comprising, exposing an animal having immunocompetent cells to an immunogen comprising at least an antigenic portion of a Bbtox1 polypeptide under conditions such that immunocompetent cells produce antibodies directed against the antigenic portion of the Bbtox1 polypeptide. In one embodiment, the method further comprises the step of harvesting the antibodies. In an alternative embodiment, the method comprises the step of fusing the immunocompetent cells with an immortal cell line under conditions such that a hybridoma is produced. In yet another embodiment, the portion of Bbtox1 used as an immunogen to generate the antibodies is at least a portion of SEQ ID NO:2 or SEQ ID NO:4. In another embodiment, the fusion protein comprises at least a portion of the Bbtox1 protein.

The present invention provides methods for detecting Bbtox1 comprising: providing in any order, a sample suspected of containing Bbtox1, an antibody capable of specifically binding to at least a portion of the Bbtox1; mixing the samples and the antibody under conditions wherein the antibody can bind to the Bbtox1; and detecting the binding. In preferred embodiments of the methods, the sample comprises a *B. burgdorferi* culture or isolate. In other preferred embodiments, the sample is from a subject suspected of being infected with *B. burgdorferi*. The methods of the present invention encompass any method for detection.

The present invention also provides methods for detection of polynucleotides encoding at least a portion of Bbtox1 in a biological sample (such as biological fluid) comprising the steps of: a) hybridizing at least a portion of the polynucleotide sequence comprising at least fifteen nucleotides, which hybridizes under stringent conditions to at least a portion of the polynucleotide sequence selected from the group consisting of the DNA sequences set forth in SEQ ID NO:1, SEQ ID NO:3, to nucleic acid material of a biological sample, thereby forming a hybridization complex; and b) detecting the hybridization complex, wherein the presence of the complex correlates with the presence of a polynucleotide encoding at least a portion of Bbtox1 the biological sample. In one alternative embodiment of the methods, the nucleic acid material of the biological sample is amplified by the polymerase chain reaction.

The present invention also provides methods for detecting Bbtox1 comprising the steps of: a) providing a sample suspected of containing Bbtox1; and a control containing a quantitated Bbtox1; and b) comparing the test Bbtox1 in the sample with quantitated Bbtox1 in the control to determine the relative concentration of the test Bbtox1 in the sample. In addition, the methods may be conducted using any suitable means to determine the relative concentration of Bbtox1 in the test and control samples, including but not limited to the means selected from the group consisting of Western blot analysis, Northern blot analysis, Southern blot analysis, denaturing polyacrylamide gel eletrophoresis (e.g., SDS PAGE), reverse transcriptase-coupled polymerase chain reaction (RI-PCR), enzyme-linked immunosorbent assay (ELISA or ELA), radioimmunoassay (RIA), and fluorescent immunoassay (FIA). Thus, the methods may be conducted to determine the presence of Bbtox1 in the genome of the source of the test sample, or the expression of Bbtox1 (mRNA or protein), as well as detect the presence of abnormal or mutated Bbtox1 proteins or gene sequences in the test samples.

In one preferred embodiment, the presence of Bbtox1 is detected by immunochemical analysis. For example, the immunochemical analysis can comprise detecting the binding of an antibody specific for an epitope of Bbtox1 (e.g., at least a portion of the protein encoded by SEQ ID NO:1, SEQ ID NO:3). In another preferred embodiment of the method, the antibody comprises polyclonal antibodies, while in another preferred embodiment, the antibody comprises monoclonal antibodies.

According to another aspect of the invention, a method for determining the level of Tptox1 expression in a sample is provided. The method involves measuring expression of Tptox1 in a test sample, and comparing the measured expression of Tptox1 in the test sample to a control, as a measure of the level of Tptox1 expression. The control can be a negative control, or a quantitated control of Tptox1 expression. In one embodiment, the test sample is obtained from a subject suspected of being infected with *T. pallidum*. In certain embodiments, the test sample is a *T. pallidum* culture or isolate. Expression of Tptox1 in the test sample can be Tptox1 mRNA expression and/or Tptox1 polypeptide expression. In some embodiments, Tptox1 mRNA expression can be measured using the Polymerase Chain Reaction and/or northern blotting. In certain embodiments, Tptox1 polypeptide expression can be measured using monoclonal and/or polyclonal antisera to Tptox1. In further embodiments, the test sample can be tissue or a biological fluid.

The present invention also provides methods for producing anti-Tptox1 antibodies comprising, exposing an animal having immunocompetent cells to an immunogen comprising at least an antigenic portion of a Tptox1 polypeptide under conditions such that immunocompetent cells produce antibodies directed against the antigenic portion of the Tptox1 polypeptide. In one embodiment, the method further comprises the step of harvesting the antibodies. In an alternative embodiment, the method comprises the step of fusing the immunocompetent cells with an immortal cell line under conditions such that a hybridoma is produced. In yet another embodiment, the portion of Tptox1 used as an immunogen to generate the antibodies is at least a portion of SEQ ID NO:17. In another embodiment, the fusion protein comprises at least a portion of the Tptox1 protein (SEQ ID NO:18).

The present invention provides methods for detecting Tptox1 comprising: providing in any order, a sample suspected of containing Tptox1, an antibody capable of specifically binding to at least a portion of the Tptox1; mixing the samples and the antibody under conditions wherein the antibody can bind to the Tptox1; and detecting the binding. In preferred embodiments of the methods, the sample comprises a *T. pallidum* culture or isolate. In other preferred embodiments, the sample is from a subject suspected of being infected with *T. pallidum*. The methods of the present invention encompass any method for detection.

The present invention also provides methods for detection of polynucleotides encoding at least a portion of Tptox1 in a biological sample (such as biological fluid) comprising the steps of: a) hybridizing at least a portion of the polynucleotide sequence comprising at least fifteen nucleotides, which hybridizes under stringent conditions to at least a portion of the polynucleotide sequence of SEQ ID NO:17, to nucleic acid material of a biological sample, thereby forming a hybridization complex; and b) detecting the hybridization complex, wherein the presence of the complex correlates with the presence of a polynucleotide encoding at least a portion of Tptox1 the biological sample. In one alternative embodiment of the methods, the nucleic acid material of the biological sample is amplified by the polymerase chain reaction.

The present invention also provides methods for detecting Tptox1 comprising the steps of: a) providing a sample suspected of containing Tptox1; and a control containing a quantitated Tptox 1; and b) comparing the test Tptox 1 in the sample with quantitated Tptox1 in the control to determine the relative concentration of the test Tptox1 in the sample. In addition, the methods may be conducted using any suitable means to determine the relative concentration of Tptox1 in the test and control samples, and such means are as described above in relation to Bbtox1 detection.

In one preferred embodiment, the presence of Tptox1 is detected by immunochemical analysis. For example, the immunochemical analysis can comprise detecting the binding of an antibody specific for an epitope of Tptox1 (e.g., at least a portion of the protein encoded by SEQ ID NO:18). In another preferred embodiment of the method, the antibody comprises polyclonal antibodies, while in another preferred embodiment, the antibody comprises monoclonal antibodies.

In other preferred embodiments of the present invention, antibodies directed against full-length or fragments of Bbtox1 are used therapeutically. In one preferred embodiment, these antibodies are administered as passive immunization against the deleterious effects of infection with *B. burgdorferi*.

In further preferred embodiments of the present invention, antibodies directed against full-length or fragments of Tptox1 are also used therapeutically. In one preferred embodiment, these antibodies are administered as passive immunization against the deleterious effects of infection with *T. pallidum*.

The present invention further provides a vaccine preparation comprising inactivated (non-toxic) Bbtox1 protein (or Tptox1) protein (i.e., as a toxoid preparation). It is contemplated that such Bbtox1 (or Tptox1) toxoid preparations will be used alone, as well as in combination with other preparations suitable for vaccine use.

In an alternative embodiment, the present invention provides a vaccine comprising a fusion protein, said fusion protein comprising a non-toxin protein sequence and at least a portion of Bbtox1. In certain embodiments Bbtox1 is encoded by the nucleic acid of SEQ ID NO:1, 3, or fragments thereof. In some embodiments Tptox1 is encoded by the nucleic acid of SEQ ID NO:17, or fragments thereof. The vaccine may be a monovalent vaccine [i.e., containing only a Bbtox1 (or Tptox1) fusion protein], a bivalent vaccine [i.e., containing both a Bbtox1 (or Tptox1) fusion protein and one other component] or a trivalent or higher valency vaccine. In a preferred embodiment, the Bbtox1 fusion protein is combined with a fusion protein comprising a non-toxin protein sequence and at least a portion of Bbotxl. The present invention is not limited by the nature of the portion of the Bbtox1 selected. In another preferred embodiment, the Tptox1 fusion protein is combined with a fusion protein comprising a non-toxin protein sequence and at least a portion of Tptox1. The present invention is not limited by the nature of the portion of the Tptox1 selected. The present invention is also not limited by the nature of the non-toxin protein sequence employed. In a preferred embodiment, the non-toxin protein sequence comprises a poly-histidine tract. A number of alternative fusion tags or fusion partners are known in the art (e.g., MBP, GST, protein A, etc.) and may be employed for the generation of fusion proteins comprising vaccines. When a fusion partner (i.e., the non-toxin protein sequence) is employed for the production of a recombinant Bbtox1 (Tptox1) protein, the fusion partner may be removed from the recombinant Bbtox1 (Tptox1) protein if desired (i.e., prior to administration of the protein to a subject) using a variety of methods known to the art (e.g., digestion of fusion proteins containing Factor Xa or thrombin recognition sites with the appropriate enzyme). For example, a number of the pETH vectors provide an N-terminal his-tag followed by a Factor Xa cleavage site. In a preferred embodiment, the vaccine is substantially endotoxin-free.

The present invention is not limited by the method employed for the generation of vaccine comprising fusion proteins comprising a non-toxin protein sequence and at least a portion of Bbtox1. The fusion proteins may be produced by recombinant DNA means using either native or synthetic genes sequences expressed in a host cell. The present invention is also not limited to the production of vaccines using recombinant host cells; cell free in vitro transcription/translation systems may be employed for the expression of the nucleic acid constructs encoding the fusion proteins of the present invention. An example of such a cell-free system is the commercially available TnT™ Coupled Reticulocyte Lysate System (Promega). Alternatively, the fusion proteins of the present invention may be generated by synthetic means (i.e., peptide synthesis).

According to another aspect of the invention, a pharmaceutical composition is provided. The pharmaceutical composition comprises an isolated polypeptide encoded by the foregoing isolated nucleic acid molecules of the invention, in an immunogenically effective amount to induce antibody production in an immunocompetent subject against at least one antigenic portion of said isolated polypeptide, and a pharmaceutically acceptable carrier. In certain embodiments, the isolated polypeptide is a polypeptide selected from the group consisting of a polypeptide having a sequence of amino acids 1–319 of SEQ ID NO:2, a polypeptide having a sequence of amino acids 1–319 of SEQ ID NO:4, a polypeptide having a sequence of amino acids consisting of an immunogenic portion of the polypeptide of SEQ ID NO:2, a polypeptide having a sequence of amino acids consisting of an immunogenic portion of the polypeptide of SEQ ID NO:4, a polypeptide having a sequence of amino acids 1–254 of SEQ ID NO:18, and a polypeptide having a sequence of amino acids consisting of an immunogenic portion of the polypeptide of SEQ ID NO:18. In important embodiments, the isolated polypeptide is substantially endotoxin-free.

According to another aspect of the invention, a pharmaceutical composition is provided. The pharmaceutical composition comprises a Bbtox1 vaccine in an immunogenically effective amount to induce antibody production in an immunocompetent subject against at least one Bbtox1 immunogenic portion of said vaccine, and a pharmaceutically acceptable carrier. In important embodiments, the Bbtox1 vaccine is substantially endotoxin-free.

According to a further aspect of the invention, a pharmaceutical composition is provided. The pharmaceutical composition comprises a Bbtox1 binding agent in a pharmaceutically effective amount to inhibit Bbtox1 toxin activity, and a pharmaceutically acceptable carrier. In one embodiment, the Bbtox1 binding agent is an isolated polypeptide which binds selectively a polypeptide encoded by any of the foregoing isolated nucleic acid molecules of the invention, and in relation to SEQ ID NO:1or SEQ ID NO:3 (Bbtox1). In an important embodiment, the isolated binding polypeptide binds to a polypeptide having the sequence of amino acids of SEQ ID NO:2 or SEQ ID NO:4. Preferably, the isolated binding polypeptide is an antibody or an antibody fragment selected from the group consisting of a Fab fragment, a $F(ab)_2$ fragment or a fragment including a CDR3 region selective for the polypeptide having the sequence of amino acids of SEQ ID NO:2 or SEQ ID NO:4, or of an antigenic portion thereof.

According to still another aspect of the invention, a method for inhibiting Bbtox1 activity in a subject, is provided. The method involves administering to a subject in need of such treatment a Bbtox1 binding agent in a pharmaceutically effective amount to inhibit Bbtox1 activity. Preferred Bbtox1 binding agents are as desdribed in the foregoing embodiments of the invention. In certain embodiments, the method further comprises co-administering an antibiotic and/or an antibacterial agent.

According to yet another aspect of the invention, a method for conferring Bbtox1 passive immunization in a subject is provided. The method involves administering to an immunocompetent subject in need of such treatment a Bbtox1 vaccine, in an immunogenically effective amount to induce antibody production in the subject against at least one Bbtox1 immunogenic portion of said vaccine. In one embodiment, the Bbtox1 vaccine comprises at least a portion of a Bbtox1 polypeptide. In some embodiments, the Bbtox1 vaccine comprises a fusion protein, said fusion protein comprising a non-toxin protein sequence and at least a portion of a Bbtox1 polypeptide. Preferred Bbtox1 polypeptides, non-toxin protein sequence of the fusion protein, and Bbtox1 vaccines are as described in any of the foregoing embodiments. In certain embodiments, the method further comprises co-administering an antibiotic and/or an antibacterial agent.

In further aspects, the invention provides Tptox1 compositions, methods of *T. pallidum* infection diagnosis, and treatment of diseases associated with *T. pallidum* infection (e.g., Syphilis), analogous to the foregoing teachings relating to Bbtox1 and Lyme disease.

The present invention further provides methods and compositions suitable for the identification of homologous toxins in organisms, including but not limited to other Borrelia species, Treponema species, and other spirochetes. In these embodiments, the primers and probes produced during the development of the present invention are used to identify proteins with sequence similarities to Bbtox1 and/or Tptox1. Based on these experiments, the function of these putative toxins may then be determined. It is also intended that the methods and compositions of the present invention will find use in molecular diagnostic procedures. For example, it is contemplated that the PCR methods of the present invention will find use in molecular diagnostics to identify additional strains of *B. burgdorferi* and other Borrelia, etc., capable of producing Bbtox1. It is further contemplated that the primers utilized in the development of the present invention (See, SEQ ID NOS: 19–23, and the amino acid sequences set forth in SEQ ID NOS:7–16) will find use in methods for amplification of nucleic acid present in samples suspected of containing *B. burgdorferi* and/or *T. pallidum.*

These and other aspects of the invention, as well as various advantages and utilities, will be more apparent with reference to the detailed description of the preferred embodiments.

BRIEF DESCRIPTION OF THE DRAWINGS

FIG. 2 provides a schematic of the expression construct pET30/Bbtox1, which contains the sequence for full-length Bbtox1.

FIG. 3 shows the ADP-ribosyltransferase activity of recombinant Bbtox1, native cholera toxin A subunit (CTA), and lysed Borrelia.

BRIEF DESCRIPTIN OF THE SEQUENCES

Figure 1A:
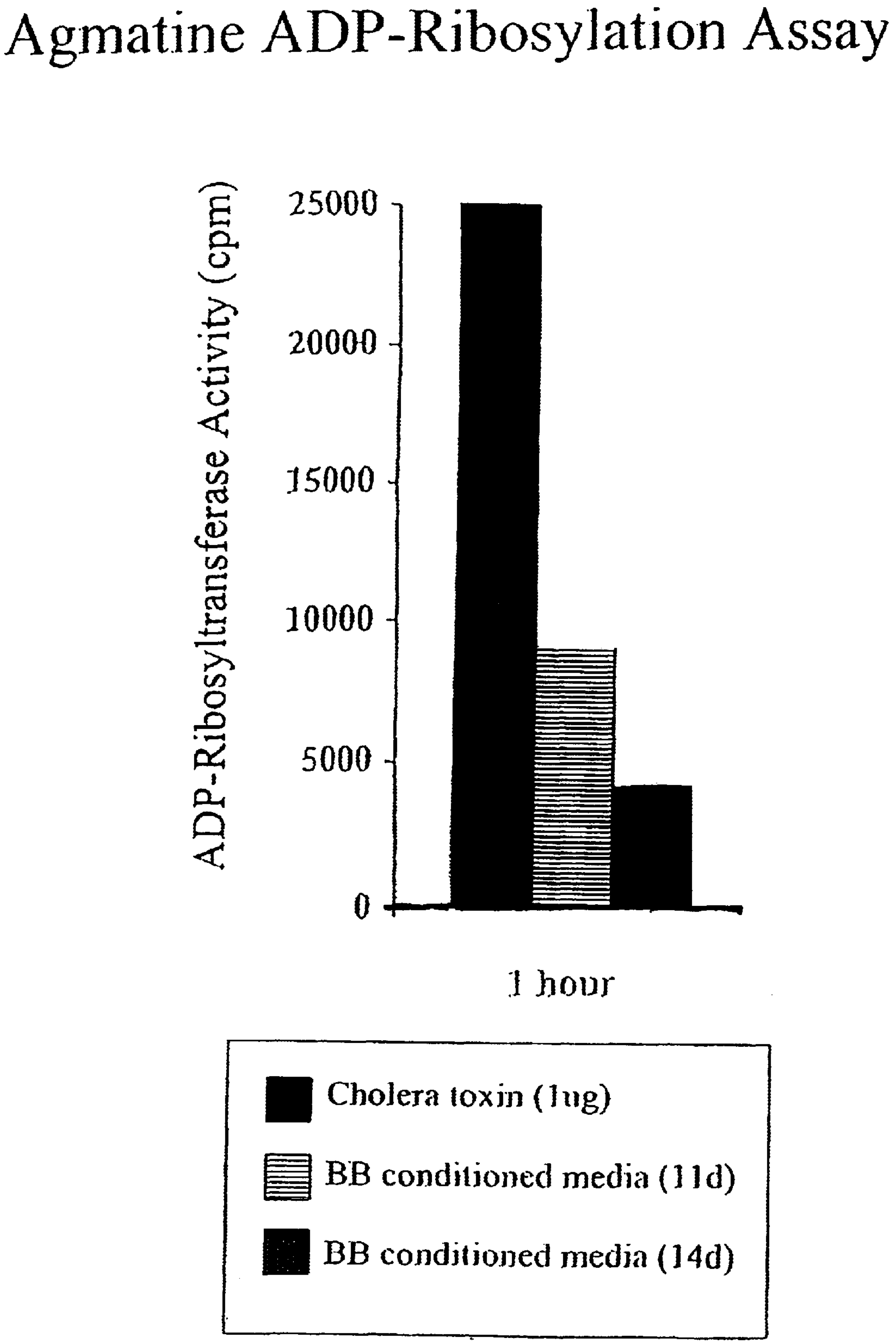
FIGS. 1A–B shows bioassay results, with Panel A providing results for assays using the agmatine ADP-ribosylation assay and Panel B providing results for assays using the EF-2 ADP-ribosylation assay.

SEQ ID NO:1is the nucleotide sequence of the Bbtox1 CDNA, *B. burgdorferi* strain B31 (gene BB0755 from GenBank Acc. No. AE001175).

SEQ ID NO:2 is the predicted amino acid sequence of the translation product of the Bbtox1 cDNA, *B. burgdorferi* strain B31 (SEQ ID NO:1).

SEQ ID NO:3 is the nucleotide sequence of the Bbtox1 cDNA, *B. burgdorferi* strain 2591.

SEQ ID NO:4 is the predicted amino acid sequence of the translation product of the Bbtox1 cDNA, *B. burgdorferi* strain 2591 (SEQ ID NO:2).

SEQ ID NO:5 is the nucleotide sequence of nucleotides 879 to 888 of SEQ ID NO:1.

SEQ ID NO:6 is the nucleotide sequence of nucleotides 879 to 888 of SEQ ID NO:2.

SEQ ID NO:7 is the amino sequence of an arbitrary Region I of a *Vibrio cholerae* ADP-ribosylating toxin.

SEQ ID NO:8 is the amino sequence of an arbitrary Region 2 of the *Vibrio cholerae* ADP-ribosylating toxin utilized in generating the amino acid sequence of SEQ ID NO:7.

SEQ ID NO:9 is the amino sequence of an arbitrary Region 1 of a *Escherichia coli* ADP-ribosylating toxin.

SEQ ID NO:10 is the amino sequence of an arbitrary Region 2 of the *Escherichia coli* ADP-ribosylating toxin utilized in generating the amino acid sequence of SEQ ID NO:9.

SEQ ID NO:11 is the amino sequence of an arbitrary Region 1 of a *Bordetella pertussis* ADP-ribosylating toxin.

SEQ ID NO:12 is the amino sequence of an arbitrary Region 2 of the *Bordetella pertussis* ADP-ribosylating toxin utilized in generating the amino acid sequence of SEQ ID NO:11.

SEQ ID NO:13 is the amino sequence of an arbitrary Region 1 of a *Pseudomonas aeruginosa* ADP-ribosylating toxin.

SEQ ID NO:14 is the amino sequence of an arbitrary Region 2 of the *Pseudomonas aeruginosa* ADP-ribosylating toxin utilized in generating the amino acid sequence of SEQ ID NO:13.

SEQ ID NO:15 is the amino sequence of an arbitrary Region 1 of a *Corynebacterium diphtheria* ADP-ribosylating toxin.

SEQ ID NO:16 is the amino sequence of an arbitrary Region 2 of the *Corynebacterium diphtheria* ADP-ribosylating toxin utilized in generating the amino acid sequence of SEQ ID NO:15.

SEQ ID NO:17 is the nucleotide sequence of a *Treponema pallidum* cDNA, Tptox1, (gene TP0819 from GenBank Acc. No. AE001252).

SEQ ID NO:18 is the predicted amino acid sequence of the translation product of the *Treponema pallidum* Tptox1 cDNA of SEQ ID NO:17).

SEQ ID NO:19 is the nucleotide sequence of a degenerate primer useful in the amplification of Bbtox1 from *B. burgdorferi.*

SEQ ID NO:20 is the nucleotide sequence of a degenerate primer useful in the amplification of Bbtox1 from *B. burgdorferi.*

SEQ ID NO:21 is the nucleotide sequence of a degenerate primer useful in the amplification of Bbtox1 from *B. burgdorferi.*

SEQ ID NO:22 is the nucleotide sequence of a degenerate primer useful in the amplification of Bbtox1 from *B. burgdorferi.*

SEQ ID NO:23 is the nucleotide sequence of a degenerate primer useful in the amplification of Bbtox1 from *B. burgdorferi.*

DETAILED DESCRIPTION OF THE INVENTION

The present invention provides compositions and methods related to *Borrelia burgdorferi* toxins. In particular, the present invention provides methods and compositions for the diagnosis, treatment and prevention of Lyme disease and/or Syphilis.

The present invention provides significant advantages and improvements over existing methods, devices, and materials related to Lyme disease. For example, as indicated above, the diagnosis of Lyme disease is often hampered by the absence of reliable tests. In addition, after initial skin infection, cultures for *B. burgdorferi* are rarely positive. PCR-DNA tests for OspA and other gene determinants are also rarely positive with blood, urine and spinal fluid. Furthermore, serologic tests are generally unreliable (Donta, et al., *Clin. Infect. Dis.*, 25:552–555 (1997)). ELISA and Western blot immunoanalyses are likewise unreliable indicators of current or past infection. Thus, new tests, such as those of the present invention provide important methods and compositions for improving the diagnostic accuracy, treatment, and prevention of Lyme disease.

The compositions and methods of the present invention provide means to prevent Lyme disease through vaccine development and utilization, as well as diagnose Lyme disease in subjects suspected of being exposed to *B. burgdorferi.* In particular, the present invention provides the full-length sequence of a *B. burgdorferi* toxin, a toxin that has not been previously identified. While an understanding of the mechanism is not necessary in order to make or use the present invention, it is contemplated that this toxin may play a role in the pathogenesis of Lyme disease. Furthermore, the isolation and purification of the toxin provides methods and compositions for preventing Lyme disease through passive antibody therapy. For example, it is contemplated that the Bbtox1 of the present invention will find use in development of antitoxins suitable for use in approaches to treat Lyme disease.

The compositions and methods of the present invention provide means to prevent Syphilis through vaccine development and utilization, as well as diagnose Syphilis in subjects suspected of being exposed to *T. pallidum*. In particular, the present invention provides the full-length sequence of a *T. pallidum* toxin, a toxin that has not been previously identified. While an understanding of the mechanism is not necessary in order to make or use the present invention, it is contemplated that this toxin may play a role in the pathogenesis of Syphilis. Furthermore, the isolation and purification of the toxin provides methods and compositions for preventing Syphilis through passive antibody therapy. For example, it is contemplated that the Tptox1 of the present invention will find use in development of antitoxins suitable for use in approaches to treat Syphilis.

As used herein, a subject is a human, non-human primate, cow, horse, pig, sheep, goat, dog, cat or rodent.

Analysis of the sequence by comparison to nucleic acid and protein databases show that Bbtox1 shares a limited homology (55% at the amino acid level) to Tptox1 (SEQ ID NO:18).

The invention thus involves in one aspect an isolated Bbtox1 polypeptide, the cDNA encoding this polypeptide, an isolated Tptox1 polypeptide, the cDNA encoding this polypeptide, functional modifications and variants of the foregoing, useful fragments of the foregoing, as well as diagnostics and therapeutics relating thereto.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein with respect to polypeptides, the term "isolated" means separated from its native environment in sufficiently pure form so that it can be manipulated or used for any one of the purposes of the invention. Thus, isolated means sufficiently pure to be used (i) to raise and/or isolate antibodies, (ii) as a reagent in an assay, or (iii) for sequencing, etc.

According to the invention, isolated nucleic acid molecules that code for a Bbtox1 and/or Tptox1 polypeptide include: (a) nucleic acid molecules which hybridize under stringent conditions to a molecule selected from the group consisting of a nucleic acid of SEQ ID NO:1, SEQ ID NO:3 (Bbtox1) and/or SEQ ID NO:17 (Tptox1), and which code for a Bbtox1 and/or Tptox1 polypeptide respectively, (b) deletions, additions and substitutions of (a) which code for a respective Bbtox1 and/or Tptox1 polypeptide, (c) nucleic acid molecules that differ from the nucleic acid molecules of (a) or (b) in codon sequence due to the degeneracy of the genetic code, and (d) full-length complements of (a), (b) or (c).

Homologs and alleles of the Bbtox1 and/or Tptox1 nucleic acids of the invention can be identified by conventional techniques. Thus, an aspect of the invention is those nucleic acid sequences which code for Bbtox1 polypeptides and which hybridize to a nucleic acid molecule consisting of the coding region of SEQ ID NO:1and/or SEQ ID NO:3 SEQ ID NO:17, under stringent conditions. Another aspect of the invention is those nucleic acid sequences which code for Tptox1 polypeptides and which hybridize to a nucleic acid molecule consisting of the coding region of SEQ ID NO:17, under stringent conditions. The term "stringent conditions" as used herein refers to parameters with which the art is familiar. Nucleic acid hybridization parameters may be found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. More specifically, stringent conditions, as used herein, refers, for example, to hybridization at 65° C. in hybridization buffer (3.5×SSC, 0.02% Ficoll, 0.02% polyvinyl pyrolidone, 0.02% Bovine Serum Albumin, 2.5 mM $NaH_2PO_4$(pH7), 0.5% SDS, 2 mM EDTA). SSC is 0.15M sodium chloride/0.15M sodium citrate, pH7; SDS is sodium dodecyl sulphate; and EDTA is ethylenediaminetetracetic acid. After hybridization, the membrane upon which the DNA is transferred is washed at 2×SSC at room temperature and then at 0.1×SSC/0.1×SDS at temperatures up to 68° C.

There are other conditions, reagents, and so forth which can be used, and would result in a similar degree of stringency. The skilled artisan will be familiar with such conditions, and thus they are not given here. It will be understood, however, that the skilled artisan will be able to manipulate the conditions in a manner to permit the clear identification of homologs and alleles of Bbtox1 nucleic acids of the invention. The skilled artisan also is familiar with the methodology for screening cells and libraries for expression of such molecules which then are routinely isolated, followed by isolation of the pertinent nucleic acid molecule and sequencing.

In general homologs and alleles typically will share at least 40% nucleotide identity and/or at least 50% amino acid identity to SEQ ID NO:1 and SEQ ID NO:2 (and/or SEQ ID NO:3 and SEQ ID NO:4, and/or or SEQ ID NO:17 and SEQ ID NO:18), respectively, in some instances will share at least 50% nucleotide identity and/or at least 65% amino acid identity and in still other instances will share at least 60% nucleotide identity and/or at least 75% amino acid identity. The homology can be calculated using various, publicly available software tools developed by NCBI (Bethesda, Md.) that can be obtained through the internet (ftp:/ncbi.nlm.nih.gov/pub/). Exemplary tools include the BLAST system available at http://wwww.ncbi.nlm.nih.gov. Pairwise and ClustalW alignments (BLOSUM30 matrix setting) as well as Kyte-Doolittle hydropathic analysis can be obtained using the MacVetor sequence analysis software (Oxford Molecular Group). Watson-Crick complements of the foregoing nucleic acids also are embraced by the invention.

In screening for Bbtox1 and/or Tptox1 related genes, such as homologs and alleles of Bbtox1 and/or Tptox1, a Southern blot may be performed using the foregoing conditions, together with a radioactive probe. After washing the membrane to which the DNA is finally transferred, the membrane can be placed against X-ray film or a phosphoimager plate to detect the radioactive signal.

The invention also includes degenerate nucleic acids which include alternative codons to those present in the native materials. For example, serine residues are encoded by the codons TCA, AGT, TCC, TCG, TCT and AGC. Each of the six codons is equivalent for the purposes of encoding a serine residue. Thus, it will be apparent to one of ordinary skill in the art that any of the serine-encoding nucleotide triplets may be employed to direct the protein synthesis apparatus, in vitro or in vivo, to incorporate a serine residue into an elongating Bbtox1 polypeptide. Similarly, nucleotide sequence triplets which encode other amino acid residues include, but are not limited to: CCA, CCC, CCG and CCT (proline codons); CGA, CGC, CGG, CGT, AGA and AGG (arginine codons); ACA, ACC, ACG and ACT (threonine codons); AAC and AAT (asparagine codons); and ATA, ATC and ATT (isoleucine codons). Other amino acid residues may be encoded similarly by multiple nucleotide sequences. Thus, the invention embraces degenerate nucleic acids that differ from the biologically isolated nucleic acids in codon sequence due to the degeneracy of the genetic code.

The invention also provides isolated unique fragments of SEQ ID NO:1, SEQ ID NO:3 and/or SEQ ID NO:17 or complements of thereof. A unique fragment is one that is a ‘signature’ for the larger nucleic acid. For example, the unique fragment is long enough to assure that its precise sequence is not found in molecules within the human genome outside of the Bbtox1 nucleic acids defined above (and human alleles). Those of ordinary skill in the art may apply no more than routine procedures to determine if a fragment is unique within the human genome. Unique fragments, however, exclude fragments completely composed of the nucleotide sequences of any of GenBank accession numbers listed in Table I below, or other previously published sequences as of the filing date of this application.

TABLE 1

| Sequences with partial homologies to Bbtox1 |
|---|
| Sequences with GenBank accession numbers: AE000783, AE001175, and AE001252 |

A fragment which is completely composed of the sequence described in the foregoing GenBank deposits is one which does not include any of the nucleotides unique to the sequences of the invention. Thus, a unique fragment must contain a nucleotide sequence other than the exact sequence of those in GenBank or fragments thereof. The difference may be an addition, deletion or substitution with respect to the GenBank sequence or it may be a sequence wholly separate from the GenBank sequence.

Unique fragments can be used as probes in Southern and Northern blot assays to identify such nucleic acids, or can be used in amplification assays such as those employing PCR. As known to those skilled in the art, large probes such as 200, 250, 300 or more nucleotides are preferred for certain uses such as Southern and Northern blots, while smaller fragments will be preferred for uses such as PCR. Unique fragments also can be used to produce fusion proteins for generating antibodies or determining binding of the polypeptide fragments, as demonstrated in the Examples, or for generating immunoassay components. Likewise, unique fragments can be employed to produce nonfused fragments of the Bbtox1 polypeptides, useful, for example, in the preparation of antibodies, immunoassays or therapeutic applications. Unique fragments further can be used as antisense molecules to inhibit the expression of Bbtox1 nucleic acids and polypeptides respectively.

As will be recognized by those skilled in the art, the size of the unique fragment will depend upon its conservancy in the genetic code. Thus, some regions of SEQ ID NO:1, SEQ ID NO:3, or SEQ ID NO:17 and complements will require longer segments to be unique while others will require only short segments, typically between 12 and 32 nucleotides long (e.g. 12, 13, 14, 15, 16, 17, 18, 19, 20, 21, 22, 23, 24, 25, 26, 27, 28, 29, 30, 31 and 32 bases) or more, up to the entire length of the disclosed sequence . As mentioned above, this disclosure intends to embrace each and every fragment of each sequence, beginning at the first nucleotide, the second nucleotide and so on, up to 8 nucleotides short of the end, and ending anywhere from nucleotide number 8, 9, 10 and so on for each sequence, up to the very last nucleotide, (provided the sequence is unique as described above). Virtually any segment of the region of SEQ ID NO:1 beginning at nucleotide 1 and ending at nucleotide 957, or SEQ ID NO:3 beginning at nucleotide 1 and ending at nucleotide 957, or SEQ ID NO:17 beginning at nucleotide 1 and ending at nucleotide 762, or complements thereof, that is 20 or more nucleotides in length will be unique. Those skilled in the art are well versed in methods for selecting such sequences, typically on the basis of the ability of the unique fragment to selectively distinguish the sequence of interest from other sequences in the human genome of the fragment to those on known databases typically is all that is necessary, although in vitro confirmatory hybridization and sequencing analysis may be performed.

The invention also involves expression vectors coding for Bbtox1, or Tptox1, proteins and fragments and variants thereof and host cells containing those expression vectors. Virtually any cells, prokaryotic or eukaryotic, which can be transformed with heterologous DNA or RNA and which can be grown or maintained in culture, may be used in the practice of the invention. Examples include bacterial cells such as *E.coli* and mammalian cells such as mouse, hamster, pig, goat, primate, etc. They may be of a wide variety of tissue types, including mast cells, fibroblasts, oocytes and lymphocytes, and they may be primary cells or cell lines. Specific examples include CHO cells and COS cells. Cell-free transcription systems also may be used in lieu of cells.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is furrther characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region which includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding Bbtox1 polypeptide or fragment or variant thereof. That heterologous DNA (RNA) is placed under operable control of transcriptional elements to permit the expression of the heterologous DNA in the host cell.

Preferred systems for mRNA expression in mammalian cells are those such as pRc/CMV (available from Invitrogen, Carlsbad, Calif.) that contain a selectable marker such as a gene that confers G418 resistance (which facilitates the selection of stably transfected cell lines) and the human cytomegalovirus (CMV) enhancer-promoter sequences. Additionally, suitable for expression in primate or canine cell lines is the pCEP4 vector (Invitrogen, Carlsbad, Calif.), which contains an Epstein Barr virus (EBV) origin of replication, facilitating the maintenance of plasmid as a multicopy extrachromosomal element. Another expression vector is the pEF-BOS plasmid containing the promoter of polypeptide Elongation Factor 1α, which stimulates efficiently transcription in vitro. The plasmid is described by Mishizuma and Nagata (*Nuc. Acids Res.* 18:5322, 1990), and its use in transfection experiments is disclosed by, for example, Demoulin (*Mol. Cell. Biol.* 16:4710–4716, 1996). Still another preferred expression vector is an adenovirus, described by Stratford-Perricaudet, which is defective for E1 and E3 proteins (*J. Clin. Invest.* 90:626–630, 1992). The use of the adenovirus as an Adeno.P1A recombinant is disclosed by Warnier et al., in intradermal injection in mice for immunization against P1A (*Int. J. Cancer*, 67:303–310, 1996).

The invention also embraces so-called expression kits, which allow the artisan to prepare a desired expression vector or vectors. Such expression kits include at least separate portions of each of the previously discussed coding sequences. Other components may be added, as desired, as long as the previously mentioned sequences, which are required, are included.

It will also be recognized that the invention embraces the use of the above described, Bbtox1 cDNA sequence containing expression vectors, to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as mouse, hamster, pig, goat, primate, etc. They may be of a wide variety of tissue types, and include primary cells and cell lines. Specific examples include dendritic cells, U293 cells, peripheral blood leukocytes, bone marrow stem cells and embryonic stem cells.

The invention also provides isolated polypeptides (including whole proteins and partial proteins), encoded by the foregoing Bbtox1 nucleic acids, and include the polypeptides of SEQ ID NO:2 and/or SEQ ID NO:4, and unique fragments thereof. Such polypeptides are useful, for example, alone or as fusion proteins that can be used as vaccines against Lyme disease. The invention further provides isolated polypeptides (including whole proteins and partial proteins), encoded by the foregoing Tptox1 nucleic acids, and include the polypeptide of SEQ ID NO:18, and unique fragments thereof. Such polypeptides are useful, for example, alone or as fusion proteins that can be used as vaccines against Syphilis. Polypeptides can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as are presented by MHC molecules on the surface of a cell for immune recognition) also can be synthesized chemically using well-established methods of peptide synthesis.

A unique fragment of an Bbtox1, or Tptox1, polypeptide, in general, has the features and characteristics of unique fragments as discussed above in connection with nucleic acids. As will be recognized by those skilled in the art, the size of the unique fragment will depend upon factors such as whether the fragment constitutes a portion of a conserved protein domain. Thus, some regions of SEQ ID NO:2, SEQ ID NO:4, and/or SEQ ID NO:18 will require longer segments to be unique while others will require only short segments, typically between 5 and 12 amino acids [e.g. 5, 6, 7, 8, 9, 10, 11 and 12 amino acids long or more, including each integer up to the full length, 319 (Bbtox1) or 254 (Tptox1) amino acids long]. Virtually any segment of SEQ ID NO:2, SEQ ID NO:4, and/or SEQ ID NO:18, that is 9 or more amino acids in length will be unique.

Unique fragments of a polypeptide preferably are those fragments which retain a distinct functional capability of the polypeptide. Functional capabilities which can be retained in a unique fragment of a polypeptide include interaction with antibodies, interaction with other polypeptides or fragments thereof. One important activity is the ability to act as a signature for identifying the polypeptide. Another is the ability to complex with HLA and to provoke in a human an immune response. Those skilled in the art are well versed in methods for selecting unique amino acid sequences, typically on the basis of the ability of the unique fragment to selectively distinguish the sequence of interest from non-family members. A comparison of the sequence of the fragment to those on known databases typically is all that is necessary.

The invention embraces variants of the Bbtox1 and/or Tptox1 polypeptides described above. As used herein, a "variant" of a Bbtox1 (or Tptox1) polypeptide is a polypeptide which contains one or more modifications to the primary amino acid sequence of a Bbtox1 (or Tptox1) polypeptide. Modifications which create a Bbtox1 polypeptide variant are typically made to the nucleic acid which encodes the Bbtox1 (or Tptox1) polypeptide, and can include deletions, point mutations, truncations, amino acid substitutions and addition of amino acids or non-amino acid moieties to: 1) reduce or eliminate an activity of a Bbtox1 (or Tptox1) polypeptide; 2) enhance a property of a Bbtox1 (or Tptox1) polypeptide, such as protein stability in an expression system or the stability of protein-protein binding; 3) provide a novel activity or property to a Bbtox1 (or Tptox1) polypeptide, such as addition of an antigenic epitope or addition of a detectable moiety; or 4) to provide equivalent or better binding to a Bbtox1 (or Tptox1) polypeptide receptor or other molecule (e.g., heparin). Alternatively, modifications can be made directly to the polypeptide, such as by cleavage, addition of a linker molecule, addition of a detectable moiety, such as biotin, addition of a fatty acid, and the like. Modifications also embrace fusion proteins comprising all or part of the Bbtox1 (or Tptox1) amino acid sequence. One of skill in the art will be familiar with methods for predicting the effect on protein conformation of a change in protein sequence, and can thus "design" a variant Bbtox1 (or Tptox1) polypeptide according to known methods. One example of such a method is described by Dahiyat and Mayo in *Science* 278:82–87, 1997, whereby proteins can be designed de novo. The method can be applied to a known protein to vary a only a portion of the polypeptide sequence. By applying the computational methods of Dahiyat and Mayo, specific variants of a cancer associated antigen polypeptide can be proposed and tested to determine whether the variant retains a desired conformation.

Variants can include Bbtox1 polypeptides which are modified specifically to alter a feature of the polypeptide unrelated to its physiological activity. For example, cysteine residues can be substituted or deleted to prevent unwanted disulfide linkages. Similarly, certain amino acids can be changed to enhance expression of a Bbtox1 (or Tptox1) polypeptide by eliminating proteolysis by proteases in an expression system (e.g., dibasic amino acid residues in yeast expression systems in which KEX2 protease activity is present).

Mutations of a nucleic acid which encodes a Bbtox1 (or Tptox1) polypeptide preferably preserve the amino acid reading frame of the coding sequence, and preferably do not create regions in the nucleic acid which are likely to hybridize to form secondary structures, such a hairpins or loops, which can be deleterious to expression of the variant polypeptide.

Mutations can be made by selecting an amino acid substitution, or by random mutagenesis of a selected site in a nucleic acid which encodes the polypeptide. Variant polypeptides are then expressed and tested for one or more activities to determine which mutation provides a variant polypeptide with the desired properties. Further mutations can be made to variants (or to non-variant Bbtox1, or Tptox1, polypeptides) which are silent as to the amino acid sequence of the polypeptide, but which provide preferred codons for translation in a particular host. The preferred codons for translation of a nucleic acid in, e.g., *E. coli*, are well known to those of ordinary skill in the art. Still other mutations can be made to the noncoding sequences of a Bbtox1 (or Tptox1) gene or cDNA clone to enhance expression of the polypeptide.

The skilled artisan will realize that conservative amino acid substitutions may be made in Bbtox1 (or Tptox1) polypeptides to provide functionally equivalent variants of the foregoing polypeptides, i.e, the variants retain the functional capabilities of the Bbtox1 (or Tptox1) polypeptides. As used herein, a "conservative amino acid substitution" refers to an amino acid substitution which does not alter the relative charge or size characteristics of the protein in which the amino acid substitution is made. Variants can be prepared according to methods for altering polypeptide sequence known to one of ordinary skill in the art such as are found in references which compile such methods, e.g. *Molecular Cloning: A Laboratory Manual*, J. Sambrook, et al., eds., Second Edition, Cold Spring Harbor Laboratory Press, Cold Spring Harbor, N.Y., 1989, or *Current Protocols in Molecular Biology*, F. M. Ausubel, et al., eds., John Wiley & Sons, Inc., New York. Exemplary functionally equivalent variants of the Bbtox1 polypeptides include conservative amino acid substitutions of SEQ ID NO:2 or SEQ ID NO:4. Exemplary functionally equivalent variants of the Tptox1 polypeptides include conservative amino acid substitutions of SEQ ID NO:18. Conservative substitutions of amino acids include substitutions made amongst amino acids within the following groups: (a) M, I, L, V; (b) F, Y, W; (c) K, R, H; (d) A, G; (e) S, T; (f) Q, N; and (g) E, D.

Thus functionally equivalent variants of Bbtox1 and/or Tptox1 polypeptides, i.e., variants of Bbtox1 and/or Tptox1 polypeptides which retain the function of the natural Bbtox1 and/or Tptox1 polypeptides, are contemplated by the invention. Conservative amino-acid substitutions in the amino acid sequence of Bbtox1 (and/or Tptox1) polypeptides to produce functionally equivalent variants of Bbtox1 (and/or Tptox1) polypeptides typically are made by alteration of a nucleic acid encoding Bbtox1 polypeptides (SEQ ID NOs:1, 3), and/or alteration of a nucleic acid encoding Tptox1 polypeptides (SEQ ID NO:17). Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488–492, 1985), or by S chemical synthesis of a gene encoding a Bbtox1 (and/or Tptox1) polypeptide. The activity of functionally equivalent fragments of Bbtox1 (and/or Tptox1) polypeptides can be tested by cloning the gene encoding the altered Bbtox1 (and/or Tptox1) polypeptide into a bacterial or mammalian expression vector, introducing the vector into an appropriate host cell, expressing the altered Bbtox1 (and/or Tptox1) polypeptide, and testing for a functional capability of the Bbtox1 (and/or Tptox1) polypeptides as disclosed herein (e.g., ADP-ribosylation activity to determine cholera toxin-like activity, etc.).

The invention as described herein has a number of uses, some of which are described elsewhere herein. First, the invention permits isolation of Bbtox1 and Tptox1 polypeptides. A variety of methodologies well-known to the skilled practitioner can be utilized to obtain isolated Bbtox1 molecules. The polypeptide may be purified from cells/organisms (e.g., *Borrelia burgdorferi, Treponema pallidum*) which naturally produce the polypeptide by chromatographic means or immunological recognition. Alternatively, an expression vector may be introduced into cells to cause production of the polypeptide. In another method, mRNA transcripts may be microinjected or otherwise introduced into cells to cause production of the encoded polypeptide. Translation of Bbtox1 and/or of Tptox1 mRNA in cell-free extracts such as the reticulocyte lysate system also may be used to produce Bbtox1 and/or Tptox1 polypeptides, respectively. Those skilled in the art also can readily follow known methods for isolating Bbtox1 and/or Tptox1 polypeptides. These include, but are not limited to, immunochromatography, HPLC, size-exclusion chromatography, ion-exchange chromatography and immune-affinity chromatography.

The invention also provides, in certain embodiments, "dominant negative" polypeptides derived from Bbtox1 and/or Tptox1 polypeptides. A dominant negative polypeptide is an inactive variant of a protein, which, by interacting with the cellular machinery, displaces an active protein from its interaction with the cellular machinery or competes with the active protein, thereby reducing the effect of the active protein. For example, a dominant negative receptor which binds a ligand but does not transmit a signal in response to binding of the ligand can reduce the biological effect of expression of the ligand. Likewise, a dominant negative catalytically-inactive kinase which interacts normally with target proteins but does not phosphorylate the target proteins can reduce phosphorylation of the target proteins in response to a cellular signal. Similarly, a dominant negative transcription factor which binds to a promoter site in the control region of a gene but does not increase gene transcription can reduce the effect of a normal transcription factor by occupying promoter binding sites without increasing transcription.

The end result of the expression of a dominant negative polypeptide in a cell is a reduction in function of active proteins. One of ordinary skill in the art can assess the potential for a dominant negative variant of a protein, and using standard mutagenesis techniques to create one or more dominant negative variant polypeptides. See, e.g., U.S. Pat. No. 5,580,723 and Sambrook et al., *Molecular Cloning: A Laboratory Manual*, Second Edition, Cold Spring Harbor Laboratory Press, 1989. The skilled artisan then can test the population of mutagenized polypeptides for diminution in a selected and/or for retention of such an activity. Other similar methods for creating and testing dominant negative variants of a protein will be apparent to one of ordinary skill in the art.

The isolation of the Bbtox1 cDNA and the Tptox1 cDNA also makes it possible for the artisan to diagnose a disorder characterized by expression of Bbtox1 (e.g., Lyme disease), or expression of Tptox1 (Syphilis). These methods involve determining expression of the Bbtox1 gene, and/or Bbtox1 polypeptides derived therefrom, and expression of the Tptox1 gene, and/or Tptox1 polypeptides derived therefrom. In the former situation, such determinations can be carried out via any standard nucleic acid determination assay, including the polymerase chain reaction, or assaying with labeled hybridization probes as exemplified below. In the latter situation, such determination can be carried out via any standard immunological assay using, for example, antibodies which bind to the secreted Bbtox1 and/or Tptox1 protein.

The invention also embraces peptide binding agents which, for example, can be antibodies or fragments of antibodies ("binding polypeptides"), having the ability to selectively bind to Bbtox1 polypeptides (e.g., SEQ ID NOs: 2 and 4), and to Tptox1 polypeptides (e.g., SEQ ID NO:18). Antibodies include polyclonal and monoclonal antibodies, prepared according to conventional methodology. In certain embodiments, the invention excludes binding agents (e.g., antibodies) that bind to the toxin polypeptides of *V. cholerae, E. coli, B. pertussis, P. aeruginosa, T. pallidum*, and/or *C. diptheriae.*

Significantly, as is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an $F(ab')_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, 1986; Roitt, 1991). In both the heavy chain Fd fragment and the light chain of IgG immunoglobulins, there are four framework regions (FRI through FR4) separated respectively by three complementarity determining regions (CDRI through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Thus, as will be apparent to one of ordinary skill in the art, the present invention also provides for $F(ab')_2$, Fab, Fv and Fd fragments; chimeric antibodies in which the Fc and/or FR and/or CDR1 and/or CDR2 and/or light chain CDR3 regions have been replaced by homologous human or non-human sequences; chimeric $F(ab')_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or non-human sequences. The present invention also includes so-called single chain antibodies.

Thus, the invention involves polypeptides of numerous size and type that bind specifically to Bbtox1 and/or Tptox1 polypeptides, complexes of both Bbtox1 polypeptides and their binding partners, and complexes of both Tptox1 polypeptides and their binding partners. These polypeptides may be derived also from sources other than antibody technology. For example, such polypeptide binding agents can be provided by degenerate peptide libraries which can be readily prepared in solution, in immobilized form, as bacterial flagella peptide display libraries or as phage display libraries. Combinatorial libraries also can be synthesized of peptides containing one or more amino acids. Libraries further can be synthesized of peptides and non-peptide synthetic moieties.

Phage display can be particularly effective in identifying binding peptides useful according to the invention. Briefly, one prepares a phage library (using e.g. m13, fd, or lambda phage), displaying inserts from 4 to about 80 amino acid residues using conventional procedures. The inserts may represent, for example, a completely degenerate or biased array. One then can select phage-bearing inserts which bind to a Bbtox1 or Tptox1 polypeptide, or a complex of Bbtox1 and a binding partner, or a complex of Tptox1 and a binding partner. This process can be repeated through several cycles of reselection of phage that bind to the polypeptide or complex. Repeated rounds lead to enrichment of phage bearing particular sequences. DNA sequence analysis can be conducted to identify the sequences of the expressed polypeptides. The minimal linear portion of the sequence that binds to the Bbtox1 polypeptide or complex can be determined. One can repeat the procedure using a biased library containing inserts containing part or all of the minimal linear portion plus one or more additional degenerate residues upstream or downstream thereof. Yeast two-hybrid screening methods also may be used to identify polypeptides that bind to the Bbtox1 or Tptox1 polypeptides. Thus, the Bbtox1 (or Tptox1) polypeptides of the invention, or a fragment thereof, or complexes of Bbtox1 (or Tptox1) and a binding partner can be used to screen peptide libraries, including phage display libraries, to identify and select peptide binding partners of the Bbtox1 (or Tptox1) polypeptides of the invention. Such molecules can be used, as described, for screening assays, for purification protocols, for interfering directly with the functioning of Bbtox1 (or Tptox1) and for other purposes that will be apparent to those of ordinary skill in the art.

A Bbtox1 (or Tptox1) polypeptide, or a fragment thereof, also can be used to isolate their native binding partners. Isolation of binding partners may be performed according to well-known methods. For example, isolated Bbtox1 polypeptides (that include Bbtox1, or Tptox1, phosporylated polypeptides) can be attached to a substrate, and then a solution suspected of containing an Bbtox1 (or Tptox1) binding partner may be applied to the substrate. If the binding partner for Bbtox1 (or Tptox1) polypeptides is present in the solution, then it will bind to the substrate-bound Bbtox1 (or Tptox1) polypeptide. The binding partner then may be isolated. Other proteins which are binding partners for Bbtox1 (or Tptox1), may be isolated by similar methods without undue experimentation.

Figure 4:
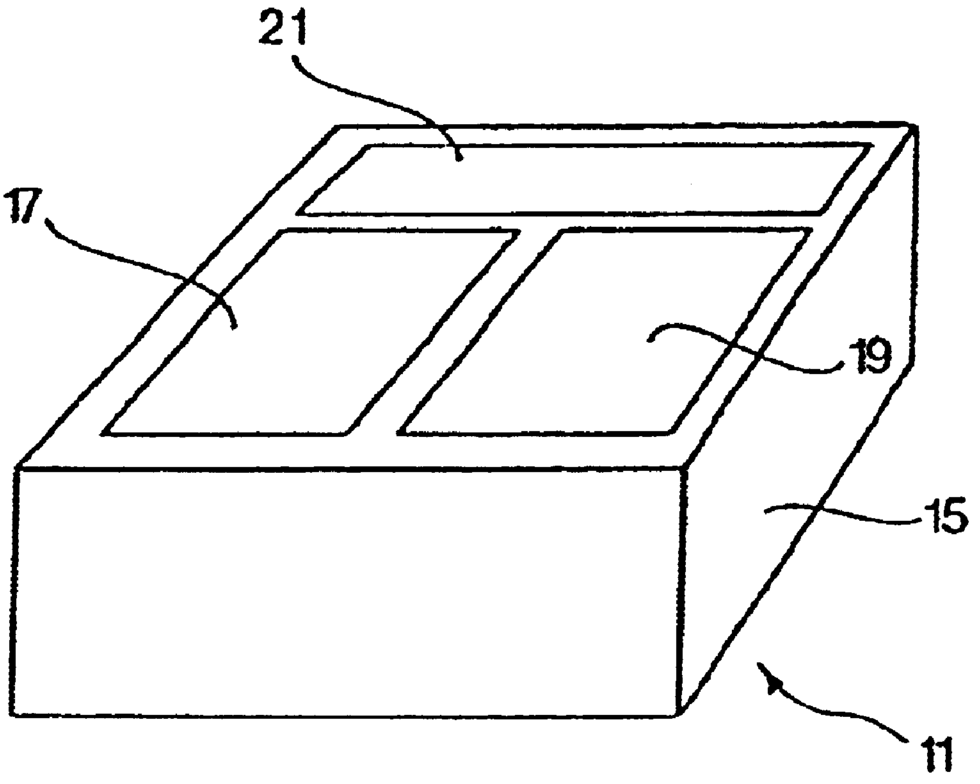
FIG. 4 depicts a kit comprising agents of the invention (e.g., anti-Bbtox1 specific antibodies, Bbtox1 epitopes, etc.), and instructions for utilizing such agents in diagnostic or therapeutic applications.

The invention also provides novel kits which could be used to measure the levels of the Bbtox1 nucleic acids of the invention, Bbtox1 expression products of the invention or anti-Bbtox1 antibodies. In the case of nucleic acid detection, pairs of primers for amplifying Bbtox1 nucleic acids can be included. The preferred kits would include controls such as known amounts of nucleic acid probes, Bbtox1 epitopes (such as Bbtox1 expression products) or anti-Bbtox1 antibodies, as well as instructions or other printed material. In certain embodiments the printed material can characterize risk of developing a cancer based upon the outcome of the assay. The reagents may be packaged in containers and/or coated on wells in predetermined amounts, and the kits may include standard materials such as labeled immunological reagents (such as labeled anti-IgG antibodies) and the like. One kit is a packaged polystyrene microtiter plate coated with Bbtox1 protein and a container containing labeled anti-human IgG antibodies. A well of the plate is contacted with, for example, serum, washed and then contacted with the anti-IgG antibody. The label is then detected. A kit embodying features of the present invention, generally designated by the numeral 11, is illustrated in FIG. 4. Kit 11 is comprised of the following major elements: packaging 15, an agent of the invention 17, a control agent 19 and instructions 21. Packaging 15 is a box-like structure for holding a vial (or number of vials) containing an agent of the invention 17, a vial (or number of vials) containing a control agent 19, and instructions 21. Individuals skilled in the art can readily modify packaging 15 to suit individual needs.

Similar kits are also provided which could be used to measure the levels of the Tptox 1 nucleic acids of the invention, Tptox1 expression products of the invention or anti-Tptox1 antibodies.

A. Detection and Identification of Toxin-producing *B. burgdorferi*

The present invention also provides methods for detecting Bbtox1 expression, including methods for quantitative analysis of toxin concentration in samples. Thus, the methods of the present invention are capable of identifying samples (e.g., various *B. burgdorferi* cultures) which contain expressed Bbtox1 protein. In one preferred embodiment, the methods may be conducted to determine the presence of Bbtox1 in the genome of the culture source of the test sample, or the expression of Bbtox (mRNA or protein), as well as detect the presence of abnormal or mutated Bbtox1 proteins or gene sequences in the test samples.

In other preferred embodiments, the presence of Bbtox1 is detected by immunochemical analysis. However, it is not intended that the present invention be limited to any particular antibody preparation. Thus, antibodies useful in the present invention include, but are not limited to polyclonals, monoclonals, chimerics, single chains, Fab fragments, and Fab expression libraries.

Various procedures known in the art may be used for the production of polyclonal antibodies to Bbtox1. For the production of antibody, various host animals can be immunized by injection with the peptide corresponding to the Bbtox1 epitope of interest, including but not limited to rabbits, mice, rats, sheep, goats, etc. In a preferred embodiment, the peptide is conjugated to an immunogenic carrier (e.g., diphtheria toxoid, bovine serum albumins (BSA), or keyhole limpet hemocyanin (KLH)). Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum.*

For preparation of monoclonal antibodies directed against Bbtox1, any technique that provides for the production of antibody molecules by continuous cell lines in culture may be used (See, e.g., Harlow and Lane, *Antibodies: A Laboratory Manual*, Cold Spring Harbor Laboratory Press, Cold Spring Harbor, N.Y. for descriptions of such methods). These include but are not limited to hybridoma technique originally developed by Köhler and Milstein (Kohler and Milstein, *Nature* 256:494–497 (1975)), as well as the trioma technique, the human B-cell hybridoma technique (See, e.g., Kozbor, et al., *Immunol. Today* 4:72 (1983)), and the EBV-hybridoma technique to produce human monoclonal antibodies (Cole, et al., in *Monoclonal Antibodies and Cancer Therapy*, Alan R. Liss, Inc., pp.77–96 (1985)).

In an additional embodiment of the invention, monoclonal antibodies can be produced in germ-free animals utilizing recent technology (See, e.g., PCT/US90/02545). According to the invention, human antibodies may be used and can be obtained by using human hybridomas (Cote, et al., *Proc. Natl. Acad. Sci USA*, 80:2026–2030 (1983)) or by transforming human B cells with EBV virus in vitro (Cole, et al., in *Monoclonal Antibodies and Cancer Therapy*, Alan R. Liss, pp. 77–96 (1985)).

According to the invention, techniques described for the production of single chain antibodies (U.S. Pat. No. 4,946,778; herein incorporated by reference) can be adapted to produce Bbtox1 single chain antibodies. An additional embodiment of the invention utilizes the techniques described for the construction of Fab expression libraries (Huse, et al., *Science* 246:1275–1281 (1989)) to allow rapid and easy identification of monoclonal Fab fragments with the desired specificity for Bbtox1.

Antibody fragments which contain the idiotype (antigen binding region) of the antibody molecule can be generated by known techniques. For example, such fragments include but are not limited to: $F(ab')_2$ fragment which can be produced by pepsin digestion of the antibody molecule; the Fab' fragments which can be generated by reducing the disulfide bridges of the $F(ab')_2$ fragment and the Fab fragments which can be generated by treating the antibody molecule with papain and a reducing agent.

In the production of antibodies, screening for the desired antibody can be accomplished by techniques known in the art, including but not limited to radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels), Western Blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.

The foregoing antibodies can be used in methods known in the art relating to the localization and structure of Btox1 (e.g., for Western blotting), measuring levels thereof in appropriate biological sample, etc. The antibodies can be used to detect Bbtox1 in a biological sample from an individual or from a culture (e.g., a culture filtrate of *B. burgdorferi*). The biological sample can be a biological fluid, such as but not limited to, blood, serum, plasma, interstitial fluid, synovial fluid, cerebrospinal fluid, urine and the like.

The biological samples can then be tested directly for the presence of Bbtox1 using an appropriate strategy (e.g., ELISA or radioimmunoassay) and format (e.g., microwells, dipsticks [e.g., as described in International Patent Publication WO 93/03367], etc.). Alternatively, proteins in the sample can be size separated (e.g., by polyacrylamide gel electrophoresis (PAGE), in the presence or not of sodium dodecyl sulfate (SIDS), and the presence of Bbtox1 detected by immunoblotting (Western blotting)). Immunoblotting techniques are generally more effective with antibodies generated against a peptide corresponding to an epitope of a protein, and hence, are particularly suited to the present invention.

It is also contemplated that bacterial toxin be detected by pouring liquid samples over immobilized antibody which is directed against the bacterial toxin. It is contemplated that the immobilized antibody will be present in or on such supports as cartridges, columns, beads, or any other solid support medium. In one embodiment, following the exposure of the liquid to the immobilized antibody, unbound toxin is substantially removed by washing. The exposure of the liquid is then exposed to a reporter substance which detects the presence of bound toxin. In a preferred embodiment the reporter substance is an enzyme, fluorescent dye, or radioactive compound attached to an antibody which is directed against the toxin (i.e., in a "sandwich" immunoassay). It is also contemplated that the detection system will be developed as necessary (e.g, the addition of enzyme substrate in enzyme systems; observation using fluorescent light for fluorescent dye systems; and quantitation of radioactivity for radioactive systems).

Any of the foregoing methodology could be used in any of the aspects of the invention involving detection and identification of toxin-producing *T. pallidum.*

The foregoing explanations of particular assay systems are presented herein for purposes of illustration only, in fulfillment of the duty to present an enabling disclosure of the invention. It is to bc understood that the present invention contemplates a variety of immunochemical assay protocols within its spirit and scope.

*B. Therapy* of *B. burgdorferi, T. pallidum* Infection/Disease and Passive Immunization The present invention contemplates antitoxin therapy for humans and other animals affected by bacterial toxins. Preferred methods of treatment are by intravenous administration or oral administration of anti-Bbtox1 and anti-Tptox antitoxins (e.g., Bbtox1 and Tptox1 binding agents). However, it is also contemplated that in some cases, other borrelial antitoxins will be administered in conjunction with anti-Bbtox1 antitoxin, and/or other Treponema antitoxins will be administered in conjunction with anti-Tptox1 antitoxin. It is further contemplated that antibiotics and/or antibacterial agents could also be co-administered.

Antibiotics and/or antibacterial agents include, but are not limited to, Acedapsone; Acetosulfone Sodium; Alamecin; Alexidine; Amdinocillin; Amdinocillin Pivoxil; Amicycline; Amifloxacin; Amifloxacin Mesylate; Amikacin; Amikacin Sulfate; Aminosalicylic acid; Aminosalicylate sodium; Amoxicillin; Amphomycin; Ampicillin; Ampicillin Sodium; Apalcillin Sodium; Apramycin; Aspartocin; Astromicin Sulfate; Avilamycin; Avoparcin; Azithromycin; Azlocillin; Azlocillin Sodium; Bacampicillin Hydrochloride; Bacitracin; Bacitracin Methylene Disalicylate; Bacitracin Zinc; Bambermycins; Benzoylpas Calcium; Berythromycin; Betamicin Sulfate; Biapenem; Biniramycin; Biphenamine Hydrochloride; Bispyrithione Magsulfex; Butikacin; Butirosin Sulfate; Capreomycin Sulfate; Carbadox; Carbenicillin Disodium; Carbenicillin Indanyl Sodium; Carbenicillin Phenyl Sodium; Carbenicillin Potassium; Carumonam Sodium; Cefaclor; Cefadroxil; Cefamandole; Cefamandole Nafate; Cefamandole Sodium; Cefaparole; Cefatrizine; Cefazaflur Sodium; Cefazolin; Cefazolin Sodium; Cefbuperazone; Cefdinir; Cefepime; Cefepime Hydrochloride; Cefetecol; Cefixime; Cefmenoxime Hydrochloride; Cefmetazole; Cefmetazole Sodium; Cefonicid Monosodium; Cefonicid Sodium; Cefoperazone Sodium; Ceforanide; Cefotaxime Sodium; Cefotetan; Cefotetan Disodium; Cefotiam Hydrochloride; Cefoxitin; Cefoxitin Sodium; Cefpimizole; Cefpimizole Sodium; Cefpiramide; Cefpiramide Sodium; Cefpirome Sulfate; Cefpodoxime Proxetil; Cefprozil; Cefroxadine; Cefsulodin Sodium; Ceftazidime; Ceftibuten; Ceftizoxime Sodium; Ceftriaxone Sodium; Cefuroxime; Cefuroxime Axetil; Cefuroxime Pivoxetil; Cefuroxime Sodium; Cephacetrile Sodium; Cephalexin; Cephalexin Hydrochloride; Cephaloglycin; Cephaloridine; Cephalothin Sodium; Cephapirin Sodium; Cephradine; Cetocycline Hydrochloride; Cetophenicol; Chloramphenicol; Chloramphenicol Palmitate; Chloramphenicol Pantothenate Complex; Chloramphenicol Sodium Succinate; Chlorhexidine Phosphanilate; Chloroxylenol; Chlortetracycline Bisulfate; Chlortetracycline Hydrochloride; Cinoxacin; Ciprofloxacin; Ciprofloxacin Hydrochloride; Cirolemycin; Clarithromycin; Clinafloxacin Hydrochloride; Clindamycin; Clindamycin Hydrochloride; Clindamycin Palmitate Hydrochloride; Clindamycin Phosphate; Clofazimine; Cloxacillin Benzathine; Cloxacillin Sodium; Cloxyquin; Colistimethate Sodium; Colistin Sulfate; Coumermycin; Coumermycin Sodium; Cyclacillin; Cycloserine; Dalfopristin; Dapsone; Daptomycin; Demeclocycline; Demeclocycline Hydrochloride; Demecycline; Denofungin; Diaveridine; Dicloxacillin; Dicloxacillin Sodium; Dihydrostreptomycin Sulfate; Dipyrithione; Dirithromycin; Doxycycline; Doxycycline Calcium; Doxycycline Fosfatex; Doxycycline Hyclate; Droxacin Sodium; Enoxacin; Epicillin; Epitetracycline Hydrochloride; Erythromycin; Erythromycin Acistrate; Erythromycin Estolate; Erythromycin Ethylsuccinate; Erythromycin Gluceptate; Erythromycin Lactobionate; Erythromycin Propionate; Erythromycin Stearate; Ethambutol Hydrochloride; Ethionamide; Fleroxacin; Floxacillin; Fludalanine; Flumequine; Fosfomycin; Fosfomycin Tromethamine; Fumoxicillin; Furazolium Chloride; Furazolium Tartrate; Fusidate Sodium; Fusidic Acid; Gentamicin Sulfate; Gloximonam; Gramicidin; Haloprogin; Hetacillin; Hetacillin Potassium; Hexedine; Ibafloxacin; Imipenem; Isoconazole; Isepamicin; Isoniazid; Josamycin; Kanamycin Sulfate; Kitasamycin; Levofuraltadone; Levopropylcillin Potassium; Lexithromycin; Lincomycin; Lincomycin Hydrochloride; Lomefloxacin; Lomefloxacin Hydrochloride; Lomefloxacin Mesylate; Loracarbef; Mafenide; Meclocycline; Meclocycline Sulfosalicylate; Megalomicin Potassium Phosphate; Mequidox; Meropenem; Methacycline; Methacycline Hydrochloride; Methenamine; Methenamine Hippurate; Methenamine Mandelate; Methicillin Sodium; Metioprim; Metronidazole Hydrochloride; Metronidazole Phosphate; Mezlocillin; Mezlocillin Sodium; Minocycline; Minocycline Hydrochloride; Mirincamycin Hydrochloride; Monensin; Monensin Sodium; Nafcillin Sodium; Nalidixate Sodium; Nalidixic Acid; Natamycin; Nebramycin; Neomycin Palmitate; Neomycin Sulfate; Neomycin Undecylenate; Netilmicin Sulfate; Neutramycin; Nifuradene; Nifuraldezone; Nifuratel; Nifuratrone; Nifurdazil; Nifurimide; Nifurpirinol; Nifurquinazol; Nifurthiazole; Nitrocycline; Nitrofurantoin; Nitromide; Norfloxacin; Novobiocin Sodium; Ofloxacin; Ormetoprim; Oxacillin Sodium; Oximonam; Oximonam Sodium; Oxolinic Acid; Oxytetracycline; Oxytetracycline Calcium; Oxytetracycline Hydrochloride; Paldimycin; Parachlorophenol; Paulomycin; Pefloxacin; Pefloxacin Mesylate; Penamecillin; Penicillin G Benzathine; Penicillin G Potassium; Penicillin G Procaine; Penicillin G Sodium; Penicillin V; Penicillin V Benzathine; Penicillin V Hydrabamine; Penicillin V Potassium; Pentizidone Sodium; Phenyl Aminosalicylate; Piperacillin Sodium; Pirbenicillin Sodium; Piridicillin Sodium; Pirlimycin Hydrochloride; Pivampicillin Hydrochloride; Pivampicillin Pamoate; Pivampicillin Probenate; Polymyxin B Sulfate; Porfiromycin; Propikacin; Pyrazinamide; Pyrithione Zinc; Quindecamine Acetate; Quinupristin; Racephenicol; Ramoplanin; Ranimycin; Relomycin; Repromicin; Rifabutin; Rifametane; Rifamexil; Rifamide; Rifampin; Rifapentine; Rifaximin; Rolitetracycline; Rolitetracycline Nitrate; Rosaramicin; Rosaramicin Butyrate; Rosaramicin Propionate; Rosaramicin Sodium Phosphate; Rosaramicin Stearate; Rosoxacin; Roxarsone; Roxithromycin; Sancycline; Sanfetrinem Sodium; Sarmoxicillin; Sarpicillin; Scopafungin; Sisomicin; Sisomicin Sulfate; Sparfloxacin; Spectinomycin Hydrochloride; Spiramycin; Stallimycin Hydrochloride; Steffimycin; Streptomycin Sulfate; Streptonicozid; Sulfabenz; Sulfabenzamide; Sulfacetamide; Sulfacetamide Sodium; Sulfacytine; Sulfadiazine; Sulfadiazine Sodium; Sulfadoxine; Sulfalene; Sulfamerazine; Sulfameter; Sulfamethazine; Sulfamethizole; Sulfamethoxazole; Sulfamonomethoxine; Sulfamoxole; Sulfanilate Zinc; Sulfanitran; Sulfasalazine; Sulfasomizole; Sulfathiazole; Sulfazamet; Sulfisoxazole; Sulfisoxazole Acetyl; Sulfisoxazole Diolamine; Sulfomyxin; Sulopenem; Sultamicillin; Suncillin Sodium; Talampicillin Hydrochloride; Teicoplanin; Temafloxacin Hydrochloride; Temocillin; Tetracycline; Tetracycline Hydrochloride; Tetracycline Phosphate Complex; Tetroxoprim; Thiamphenicol; Thiphencillin Potassium; Ticarcillin Cresyl Sodium; Ticarcillin Disodium; Ticarcillin Monosodium; Ticlatone; Tiodonium Chloride; Tobramycin; Tobramycin Sulfate; Tosufloxacin; Trimethoprim; Trimethoprim Sulfate; Trisulfapyrimidines; Troleandomycin; Trospectomycin Sulfate; Tyrothricin; Vancomycin; Vancomycin Hydrochloride; Virginiamycin; Zorbamycin.

As described above, it is contemplated that antitoxins and/or vaccine preparations of the present invention may be co-administered with an antibiotic and/or an antibacterial agent (or other antitoxins) for treating or preventing *B. burgdorferi* and/or *T. pallidum* infections. The term "co-administered," means administered substantially simultaneously with another agent. By substantially simultaneously, it is meant that an antitoxin and/or a vaccine preparation of the invention is administered to the subject close enough in time with the administration of the other agent (e.g., antibiotic, antibacterial agent, other antitoxin, etc.).

It is noted by way of background that a balance must be struck when administering antitoxins, as they are usually produced in large animals such as horses; sufficient antitoxin must be administered to neutralize the toxin, but not so much antitoxin as to increase the risk of untoward side effects. These side effects are caused by: i) patient sensitivity to foreign (e.g., horse) proteins; ii) anaphylactic or immunogenic properties of non-immunoglobulin proteins; iii) the complement fixing properties of mammalian antibodies; and/or iv) the overall burden of foreign protein administered. Those of skill in the art are familiar with methods to strike this balance.

Although it is not intended to limit the route of delivery, the present invention contemplates a method for antitoxin treatment of bacterial intoxication in which delivery of antitoxin is oral. In one embodiment, antitoxin is delivered in a solid form (e.g., tablets). In an alternative embodiment antitoxin is delivered in an aqueous solution. When an aqueous solution is used, the solution has sufficient ionic strength to solubilize antibody protein, yet is made palatable for oral administration. The delivery solution may also be buffered (e.g., carbonate buffer pH 9.5) which can neutralize stomach acids and stabilize the antibodies when the antibodies are administered orally. In one embodiment the delivery solution is an aqueous solution. In another embodiment the delivery solution is a nutritional formula. Yet another embodiment contemplates the delivery of lyophilized antibody encapsulated or microencapsulated inside acid-resistant compounds.

Methods of applying enteric coatings to pharmaceutical compounds are well known to the art (companies specializing in the coating of pharmaceutical compounds are available; for example, The Coating Place (Verona, Wis.) and AAI (Wilmington, N.C.)). Enteric coatings which are resistant to gastric fluid and whose release (i.e., dissolution of the coating to release the pharmaceutical compound) is pH dependent are commercially available (for example, the polymethacrylates Eudragit® L and Eudragit® S [Röhm GmbH]). Eudragit® S is soluble in intestinal fluid from pH 7.0; this coating can be used to micro encapsulate lyophilized antitoxin antibodies and the particles are suspended in a solution having, a pH above or below pH 7.0 for oral administration. The microparticles will remain intact and undissolved until they reach the intestines, where the intestinal pH causes them to dissolve thereby releasing the antitoxin. In this method, antitoxin is administered orally in either a delivery solution or in tablet form, in therapeutic dosage, to a subject experiencing Lyme disease, or Syphilis.

The invention also contemplates a method of treatment which can be administered prophylactically (e.g., for passive immunization of a subject known to be exposed to *B. burgdorferi, T. pallidum*, etc.). In one embodiment, antitoxin is administered orally, in a delivery solution, in therapeutic dosage, to a subject, to prevent the effects of Bbtox1 on the subject exposed to *B. burgdorferi* (or *T. pallidum*). In another embodiment, antitoxin is administered orally in solid form such as tablets or as microencapsulated particles. Microencapsulation of lyophilized antibody using compounds such as Eudragit® (Rohm GmbH) or polyethylene glycol, which dissolve at a wide range of pH units, allows the oral administration of solid antitoxin in a liquid form (i.e., a suspension) to recipients unable to tolerate administration of tablets (e.g., children or patients on feeding tubes). In one preferred embodiment the subject is a child. In another embodiment, antibody raised against whole bacterial organism is administered orally to a subject, in a delivery solution, in therapeutic dosage.

Bbtox1 and Tptox1 antitoxin and vaccine related compositions of the invention may be administered alone or in combination with the above-described drug therapies as part of a pharmaceutical composition. Such a pharmaceutical composition may include the foregoing isolated molecules of the invention in combination with any standard physiologically and/or pharmaceutically acceptable carriers which are known in the art. The compositions should be sterile and contain a therapeutically effective amount of the foregoing isolated molecules of the invention in a unit of weight or volume suitable for administration to a subject. The term "pharmaceutically-acceptable carrier" as used herein means one or more compatible solid or liquid filler, diluents or encapsulating substances which are suitable for administration into a human or other animal. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy. Pharmaceutically acceptable further means a non-toxic material that is compatible with a biological system such as a cell, cell culture, tissue, or organism. The characteristics of the carrier will depend on the route of administration. Physiologically and pharmaceutically acceptable carriers include diluents, fillers, salts, buffers, stabilizers, solubilizers, and other materials which are well known in the art.

Compositions suitable for parenteral administration conveniently comprise a sterile aqueous preparation of the foregoing isolated molecules of the invention, which are preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or di-glycerides. In addition, fatty acids such as oleic acid may be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated, and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Intramyocardial administration is preferred in patients suffering form myocardial infaction. Oral administration will be preferred for prophylactic treatment because of the convenience to the patient as well as the dosing schedule.

The pharmaceutical compositions may conveniently be presented in unit dosage form and may be prepared by any of the methods well-known in the art of pharmacy. All methods include the step of bringing the foregoing isolated molecules of the invention into association with a carrier which constitutes one or more accessory ingredients. In general, the compositions are prepared by uniformly and intimately bringing the foregoing isolated molecules of the invention into association with a liquid carrier, a finely divided solid carrier, or both, and then, if necessary, shaping the product.

Compositions suitable for oral administration may be presented as discrete units, such as capsules, tablets, lozenges, each containing a predetermined amount an isolated molecule of the invention. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the isolated molecules of the invention described above, increasing convenience to the subject and the physician. Many types of release delivery systems are available and known to those of ordinary skill in the art. They include the above-described polymeric systems, as well as polymer base systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the isolated molecules of the invention are contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

As discussed above, the invention involves methods for treating individuals with Lyme disease, at risk of developing Lyme disease, and/or treating individuals with Syphilis, or at risk of developing Syphilis. The agents are administered in immunogenically-effective amounts (vaccines) to invoke the production of protective levels of antibodies in a host upon vaccination and, thus, lower the risk of the individual developing Lyme disease or Syphilis, and/or the agents are administered in therapeutic amounts or pharmaceutically effective amounts (antitoxins) to neutralize the pathologic effects of *B. burgdorferi* toxin, or *T. pallidum* toxin in a subject.

An effective amount is a dosage of the agent sufficient to provide a medically desirable result (as described above). The effective amount will vary with the particular condition being treated, the age and physical condition of the subject being treated, the severity of the condition, the duration of the treatment, the nature of the concurrent therapy (if any), the specific route of administration and like factors within the knowledge and expertise of the health practitioner. It should be understood that the agents of the invention are used to reduce the risk of developing, or to treat Lyme disease and/or Syphilis, that is, they are used prophylactically in subjects at risk of developing Lyme disease and/or Syphilis (asymptomatic), and acutely in subjects already symptomatic for the disorder. Thus, an effective amount is that amount which can lower the risk of, slow, reverse, or perhaps prevent altogether the development of Lyme disease and/or Syphilis. It will be recognized that when the agent is used in acute circumstances, it is used to prevent one or more medically undesirable results.

Generally, doses of active compounds would be from about 0.01 mg/kg per day to 1000 mg/kg per day. It is expected that doses ranging from 50–500 mg/kg will be suitable, preferably orally and in one or several administrations per day. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

C. Vaccines Against Borrelia and Treponema Species

The invention also contemplates the generation of mono- and multi-valent vaccines for the protection of an animal (particularly humans) against Borrelia species. Of particular interest are vaccines which stimulate the production of a humoral immune response to *B. burgdorferi* in humans. The antigens comprising the vaccine preparation may be native or recombinantly produced toxin proteins from the *B. burgdorferi*, as well as other species (e.g, *B. garinii*, and *B. afzelii*). When toxin proteins are used as immunogens, they are generally modified to reduce the toxicity. This modification may be by chemical or genetic (i.e., recombinant DNA technology) means. In general, genetic detoxification (i.e., the expression of nontoxic fragments in a host cell) is preferred as the expression of nontoxic fragments in a host cell precludes the presence of intact, active toxin in the final preparation. However, when chemical modification is desired, the preferred toxin modification is formaldehyde treatment.

The invention contemplates that recombinant Bbtox1 proteins be used as antigens in mono- and multivalent vaccine preparations. Soluble, substantially endotoxin-free recombinant Bbtox1 proteins may be used individually (i.e., as monovalent vaccines) or in combination with other proteins (i.e., as a multivalent vaccine). It is contemplated that a vaccine comprising proteins (native or recombinant or a mixture thereof) be used to stimulate an immune response against various Borrelia species, including those associated with relapsing fever, as well as other spirochetal organisms. Indeed, it is contemplated that vaccines which confer immunity against Bbtox1 will be useful as a means of protecting humans and other animals from the deleterious effects of this toxin, as well as other borrelial proteins.

Within a given serotype or species of Borrelia, it is contemplated that small variations will be observed in the primary amino acid sequence of the toxins produced by these 5 organisms. The present invention contemplates fusion proteins comprising portions of Bbtox1, as well as the variants found among different strains within a given serotype. The present invention provides oligonucleotide primers which may bc used to amplify at least a portion of the toxin from various strains of Borrelia, including any number of *B. burgdorferi* strains identified from clinical (including *B. burgdorferi* isolated from non-human animals), as well as those available from such sources as the American Type Culture Collection (ATCC Manassas, Va.).

In general, chemical detoxification of bacterial toxins using agents such as formaldehyde, glutaraldehyde or hydrogen peroxide is not optimal for the generation of vaccines or antitoxins. A delicate balance must be struck between too much and too little is chemical modification. If the treatment is insufficient, the vaccine may retain residual toxicity. If the treatment is too excessive, the vaccine may lose potency due to destruction of native immunogenic determinants. Another potentially major limitation of using Bbtox1 toxoids for the generation of antitoxins or vaccines is the high production expense (e.g., related to the production of Bbtox1). For the above reasons, the development of methods for the production of nontoxic but immunogenic Bbtox1 toxin proteins is desirable.

The present invention provides methods which allow the production of soluble Bbtox1 proteins in economical host cells (e.g., *E. coli*). In addition the subject invention provides methods which allow the production of soluble Bbtox1 toxin proteins in yeast and insect cells. Further, methods for the isolation of purified soluble Bbtox1 proteins which are suitable for immunization of humans and other animals are provided. These soluble, purified preparations of Bbtox1 proteins provide the basis for improved vaccine preparations and facilitate the production of antitoxin.

When recombinant Bbtox1 protein produced in gram-negative bacteria (e.g., *E. coli*) are used as vaccines, it is purified to remove endotoxin prior to administration to a host animal. In order to vaccinate a host, an immunogenically-effective amount of purified substantially endotoxin-free recombinant Bbtox1 protein is administered in any of a number of physiologically acceptable carriers known to the art. When administered for the purpose of vaccination, the purified substantially endotoxin-free recombinant Bbtox1 protein may be used alone or in conjunction with known adjutants, including potassium alum, aluminum phosphate, aluminum hydroxide, Gerbu adjuvant (GmDP; C.C. Biotech Corp.), RIBI adjuvant (MPL; RIBI Immunochemical Research, Inc.), QS21 (Cambridge Biotech). The alum and aluminum-based adjutants are particularly preferred when vaccines are to be administered to humans; however, any adjuvant approved for use in humans may be employed. The route of immunization may be nasal, oral, intramuscular, intraperitoneal or subcutaneous.

The invention contemplates the use of soluble, substantially endotoxin-free preparations of fusion proteins comprising at least a portion of Bbtox1 as a vaccine. In one embodiment, the vaccine comprises at least a portion of Bbtox1 and a poly-histidine tract (or "histidine tag"), In a particularly preferred embodiment, a fusion protein comprising the histidine -tagged Bbtox1 (full-length toxin or a portion of the toxin) is expressed using the pET series of expression vectors (Novagen). The pET expression system utilizes a vector containing, the T7 promoter which encodes the fusion protein and a host cell which can be induced to express the T7 DNA polymerase (i.e., a DE3 host strain). The production of Bbtox1 fragment fusion proteins containing a histidine tract is not limited to the use of a particular expression vector and host strain. Several commercially available expression vectors and host strains can be used to express the Bbtox1 protein sequences as a fusion protein containing a histidine tract. For example, the pQE series of expression vectors (pQF8, 12, 16, 17, 18, 30, 31, 32, 40, 41, 42, 50, 51, 52, 60 and 70) (Qiagen) which are used with the host strains M15[pREP4] (Qiagen) and SGI3009[pREP4] (Qiagen), can be used to express fusion proteins containing six histidine residues at the amino-terminus of the fusion protein.

Furthermore a number of commercially available expression vectors which provide a histidine tract also provide a protease cleavage site between the histidine tract and the protein of interest (e.g., Bbtox1 sequences). Cleavage of the resulting fusion protein with the appropriate protease will remove the histidine tag from the protein of interest Bbtox1 sequences). Removal of the histidine tag may be desirable prior to administration of the recombinant Bbtox1 protein to a subject (e.g, a human).

The invention also contemplates the generation of vaccines for the protection of an animal (particularly humans) against *T. pallidum*, utilizing the Tptox1 compositions provided by the invention, and folowing the methodology described above relating to Bbtox1.

Definitions

As used herein, the term "toxin" refers to a single protein or peptide that has deleterious effects in cells or subjects. "Bbtox1 toxin activity," "Tptox1 toxin activity," or "toxin activity" as used herein refer to the ability of a single protein or peptide (e.g., Bbtox1, Tptox1) to induce/cause cell death. In important embodiments it is neuronal cell death. In vitro, such activity can be manifested, for example, as ADP-ribosylation and/or elongation factor-2-ribosylation activity (see Examples section). In vivo, such activity is manifested according to any of the symptoms known in the art for Lyme disease and Syphilis.

As used herein, the term "neutralizing" is used in reference to antitoxins, particularly antitoxins comprising antibodies, which have the ability to prevent the pathological actions of the toxin against which the antitoxin is directed.

As used herein, the term "overproducing" is used in reference to the production of toxin polypeptides in a host cell, and indicates that the host cell is producing more of the toxin by virtue of the introduction of nucleic acid sequences encoding the toxin polypeptide than would be expressed by the host cell absent the introduction of these nucleic acid sequences. To allow ease of purification of toxin polypeptides produced in a host cell it is preferred that the host cell express or overproduce the toxin polypeptide at a level greater than 1 mg/liter of host cell culture.

As used herein, the termn "fusion protein" refers to a chimeric protein containing the protein of interest (i.e., *B. burgdorferi* Bbtox1 and/or fragments thereof, *T. pallidum* and/or fragments thereof) joined to an exogenous protein fragment (the fusion partner which consists of a non-toxin protein). The fusion partner may enhance solubility of the *B. burgdorferi* and/or *T. pallidum* protein expressed in a host cell, may provide an "affinity tag" to allow purification of the recombinant fusion protein from the host cell or culture supernatant, or both. If desired, the fusion protein may be removed from the protein of interest (i.e., to protein or fragments thereof) prior to immunization by a variety of enzymatic or chemical means known to the art.

As used herein, the term "affinity tag" refers to such structures as a "poly-histidine tract" or poly-histidine tag," or any other structure or compound which facilitates the purification of a recombinant fusion protein from a host cell, host cell culture supernatant, or both. As used herein, the term "flag tag" refers to short polypeptide marker sequence useful for recombinant protein identification and purification.

As used herein, the terms "poly-histidine tract" and "poly-histidine tag," when used in reference to a fusion protein refers to the presence of at least two histidine residues, preferably between two to ten histidine residues, at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate column.

As used herein the term "non-toxin protein" or "non-toxin protein sequence" refers to that portion of a fusion protein which comprises a protein or protein sequence which does not have toxin activity.

The term "protein of interest" as used herein refers to the protein whose expression is desired within the fusion protein. In a fusion protein the protein of interest will be joined or fused with another protein or protein domain, the fusion partner, to allow for enhanced stability of the protein of interest and/or ease of purification of the fusion protein.

As used herein the terms "protein" and "polypeptide" refer to compounds comprising, amino acids joined via peptide bonds and are used interchangeably.

As used herein, the term "chimeric protein" refers to two or more coding sequences obtained from, different genes, that have been cloned together and that, after translation, act as a single polypeptide sequence. Chimeric proteins are also referred to as "hybrid proteins." As used herein, the term "chimeric protein" refers to coding sequences that are obtained from different species of organisms, as well as coding, sequences that are obtained from the same species of organisms. Chimeric proteins may include fusin proteins as described elsewhere herein.

As used herein the term "immunogenically-effective amount" refers to that amount of an immunogen required to invoke the production of protective levels of antibodies in a host upon vaccination.

The term "protective level" when used in reference to the level of antibodies induced upon immunization of the host with an immunogen which comprises a bacterial toxin, means a level of circulating antibodies sufficient to protect the host from challenge with a lethal dose of the toxin.

As used herein, the term "therapeutic amount" or "pharmaceutically effective amount" refers to that amount of antitoxin required to neutralize the pathologic effects of *B. burgdorferi* toxin, or *T. pallidum* toxin in a subject.

As used herein, the term "purified" or "to purify" refers to the removal of contaminants from a sample. For example, antitoxins are purified by removal of contaminating non-immunoglobulin proteins; they are also purified by the removal of substantially all immunoglobulin that does not bind toxin. The removal of non-immunoglobulin proteins and/or the removal of immunoglobulins that do not bind toxin results in an increase in the percent of toxin-reactive immunglobulins in the sample. In another example, recombinant toxin polypeptides are expressed in bacterial host cells and the toxin polypeptides are purified by the removal of host cell proteins; the percent of recombinant toxin polypeptides is thereby increased in the sample.

The term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein refers to a protein which is isolated from a natural source as opposed to the production of a protein by recombinant means.

As used herein the term "portion" when in reference to a protein (as in "a portion of a given protein") refers to fragments of that protein. The fragments may range in size from four amino acid residues to the entire amino acid sequence minus one amino acid.

The terms "native gene" or "native gene sequences" are used to indicate DNA sequences encoding a particular gene which contain the same DNA sequences as found in the gene as isolated from nature. In contrast, "synthetic gene sequences" are DNA sequences which are used to replace the naturally occurring DNA sequences when the naturally occurring sequences cause expression problems in a given host cell. For example, naturally-occurring DNA sequences encoding codons which are rarely used in a host cell may be replaced (e. a., by site-directed mutagenesis) such that the synthetic DNA sequence represents a more frequently used codon. The native DNA sequence and the synthetic DNA sequence will preferably encode the same amino acid sequence.

As used herein "soluble" when in reference to a protein produced by recombinant DNA technology in a host cell, is a protein which exists in solution in the cytoplasm of the host cell; if the protein contains a single sequence, the soluble protein is exported to the periplasmic space in bacterial hosts and is secreted into the culture medium of eukaryotic cells capable of secretion or by bacterial hosts possessing the appropriate genes. In contrast, an insoluble protein is one which exists in denatured form inside cytoplasmic granules (called an inclusion bodies) in the host cell. High level expression (i.e., greater than I mg recombinant protein/liter of bacterial culture) of recombinant proteins often results in the expressed protein being found in inclusion bodies in the bacterial host cells. A soluble protein is a protein which is not found in an inclusion body inside the host cell or is found both in the cytoplasm and in inclusion bodies and in this case the protein may be present at high or low levels in the cytoplasm.

A distinction is drawn between a soluble protein (i.e., a protein which when expressed in a host cell is produced in a soluble form) and a "solubilized" protein. An insoluble recombinant protein found inside an inclusion body may be solubilized (i.e., rendered into a soluble form) by treating purified inclusion bodies with denaturants such as guanidine hydrochloride, urea or sodium dodecyl sulfate (SDS). These denaturants must then be removed from the solubilized protein preparation to allow the recovered protein to renature (i.e., refold). Not all proteins will refold into an active conformation after solubilization in a denaturant and removal of the denaturant. Many proteins precipitate upon removal of the denaturant. SDS may be used to solubilize inclusion bodies and will maintain the proteins in solution at low concentration. However, dialysis will not always remove all of the SDS (SDS can form micelles which do not dialyze out); therefore, SDS-solubilized inclusion body protein is soluble but not refolded.

As used herein, the term "reporter reagent" or "reporter molecule" is used in reference to compounds which are capable of detecting the presence of antibody bound to antigen. For example, a reporter reagent may be a colorimetric substance which is attached to an enzymatic substrate. Upon binding of antibody and anti-en, the enzyme acts on its substrate and causes the production of a color. Other reporter reagents include, but are not limited to fluorogenic and radioactive compounds or molecules.

As used herein the term "signal" is used in reference to the production of a sign that a reaction has occurred, for example, binding of antibody to antigen. It is contemplated that signals in the form of radioactivity, fluorogenic reactions, and enzymatic reactions will be used with the present invention. The signal may be assessed quantitatively as well as qualitatively.

As used herein, the term "at risk" is used in references to individuals who have been exposed to *B. burgdorferi* and may suffer the symptoms associated with infection or disease with these organisms, or individuals which travel to, or live nearby, an area that may contain the spirochete(s), or come into contact with subjects infected or suspected of being infected by the spirochete(s).

The terms "sample," "specimen," and/or "tissue" in the present specification and claims are used in their broadest sense. On the one hand, they are meant to include a specimen or culture. On the other hand, they are meant to include both biological and environmental samples. These terms encompasses all types of samples obtained from subjects, but not limited to, biological fluids fluids such as cerebrospinal fluid (CSF), synovial fluid, urine, blood, fecal matter, semen, and saliva, as well as solid tissue. The terms also encompass samples obtained from arthropods, such as ticks (e.g., gut sections and/or contents). These terms also refers to swabs and other tissue sampling, devices which are commonly used to obtain samples for culture of microorganisms.

Biological samples may be animal, including human, fluid or tissue, food products and ingredients such as dairy items, vegetables, meat and meat by-products, and waste. Environmental samples include environmental material such as surface matter, soil, water, and industrial samples, as well as samples obtained from food and dairy processing instruments, apparatus, equipment, disposable, and non-disposable items. These examples are not to be construed as limiting the sample types applicable to the present invention.

Whether biological or environmental, a sample suspected of containing microorganisms may (or may not) first be subjected to an enrichment means to create a "Pure culture" of microorganisms, By "enrichment means" or "enrichment treatment," the present invention contemplates (i) conventional techniques for isolating a particular microorganism of interest away from other microorganisms by means of liquid, solid, semi-solid or any other culture medium and/or technique, and (ii) novel techniques for isolating particular microorganisms away from other microorganisms. It is not intended that the present invention-be limited only to one enrichment step or type of enrichment means. For example, it is within the scope of the present invention, following subjecting a sample to a conventional enrichment means, to subject the resultant preparation to further purification such that a pure culture of a strain of a species of interest is produced. This pure culture may then be analyzed by the medium and method of the present invention.

As used herein, the term "culture" refers to any sample or specimen which is suspected of containing one or more microorganisms. "Pure cultures" are cultures in which the organisms present are only of one strain of a particular genus and species. This is in contrast to "mixed cultures," which are cultures in which more than one genus and/or species of microorganism are present.

As used herein, the term "organism" is used to refer to any species or type of microorganism, including but not limited to bacteria, yeasts and other fungi.

As used herein, the term "antimicrobial" is used in reference to any compound which inhibits the growth of, or kills microorganisms. It is intended that the term be used in its broadest sense, and includes, but is not limited to compounds such as antibiotics which are produced naturally or synthetically.

As used herein, the term "kit" is used in reference to a combination of reagents and other materials.

As used herein, the term "primary isolation" refers to the process of culturing organisms directly from a sample. Thus, primary isolation involves such processes as in vitro methods (e.g., inoculating agar plate with a sample), as well as inoculating an experimental animal with the sample.

As used herein, the term "isolation" refers to any cultivation of organisms, whether it be primary isolation or any subsequent cultivation, including "passage" or "transfer" of stock cultures of organisms in vitro or in vivo, for maintenance and/or use.

As used herein, the term "presumptive diagnosis" refers to a preliminary diagnosis which gives some guidance to the treating physician as to the etiologic organism involved in the patient's disease. Presumptive diagnoses are often based on "presumptive identifications," which as used herein refer to the preliminary identification of a microorganism.

As used herein, the term "definitive diagnosis" is used to refer to a final diagnosis in which the etiologic agent of the patient's disease has been identified. The term "definitive identification" is used in reference to the final identification of an organism to the genus and/or species level.

As used herein, the terms "complementary" or "complementarity" are used in reference to polynucleotides (i.e., a sequence of nucleotides) related by the basic pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous to a target under conditions of low stringency. This is not to say that conditions of low stringency arc such that non-specific binding is permitted- low stringency conditions require that the binding, of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions which promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described above.

A gene may produce multiple RNA species which are generated by differential splicing, of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other, When used in reference to a single-stranded nucleic acid sequence, the term "substantially homologous" refers to any probe which can hybridize (i.e., it is the complement of) the single-stranded nucleic acid sequence under conditions of low stringency as described above.

As used herein, the term "hybridization" is used in reference to the pairing, of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m$ 81.5+0.41(% G+C), when a nucleic acid is in aqueous solution at 1 M NaCl (See e.g., Anderson and Young, 1985, Quantitative Filter Hybridization, in Nucleic Acid Hybridization). Other references include more sophisticated computations which take structural as well as sequence characteristics into account for the calculation of $T_m$.

As used herein the term "stringency" is used in reference to the conditions of temperature, ionic strength, and the presence of other compounds such as organic solvents, under which nucleic acid hybridization's are conducted. With "high stringency" conditions, nucleic acid base pairing will occur only between nucleic acid fragments that have a high frequency of complementary base sequences. Thus, conditions of "weak" or "low" stringency are often required with nucleic acids that are derived from organisms that are genetically diverse, as the frequency of complementary sequences is usually less (see also earlier discussion).

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicas, MDV-1 RNA is the specific template for the replicas (D. L. Kacian, et al., *Proc. Natl. Acad. Sci. USA* 69:3038 (1972)). Other nucleic acid will not be replicated by this amplification enzyme. Similarly, in the case of T7 RNA polymerase, this amplification enzyme has a stringent specificity for its own promoters (M. Chamberlin, et al., *Nature* 228:227 (1970)). In the case of T4 DNA ligase, the enzyme will not ligate the two oligonucleotides or polynucleotides, where there is a mismatch between the oligonucleotide or polynucleotide substrate and the template at the ligation junction (D. Y. Wu and R. B. Wallace, *Genomics* 4:560 (1989)). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press (1989)).

As used herein, the term "amplifiable nucleic acid" is used in reference to nucleic acids which may be amplified by any amplification method. It is contemplated that "amplifiable nucleic acid" will usually comprise "sample template."

As used herein, the term "sample template" refers to nucleic acid originating from a sample which is analyzed for the presence of "target" (defined below). In contrast, "background template" is used in reference to nucleic acid other than sample template which may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refer to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems.

It is not intended that the present invention be limited to any particular detection system or label.

As used herein, the term "target," when used in reference to the polymerase chain reaction. refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerize. The two primers are complementary to their respective strands of the double stranded target sequence. To effect amplification, the mixture is denatured and the primers then annealed to their complementary sequences within the target molecule. Following annealing, the primers arc extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself axe, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the terms "restriction endonucleases" and "restriction enzymes" refer to bacterial enzymes, each of which cut double-stranded DNA at or near a specific nucleotide sequence.

The invention will be more fully understood by reference to the following examples. These examples, however, are merely intended to illustrate the embodiments of the invention and are not to be construed to limit the scope of the invention.

EXAMPLES

In the experimental disclosure which follows, the following abbreviations apply: eq (equivalents); M (Molar); μM (micromolar); N (Normal); mol (moles); mmol (millimoles); zmol (micromoles); nmol (nanomoles); g (grams); mg (milligrams); μg (micrograms); ng (nanograms); 1 or L (liters); ml (milliliters); μl (microliters); cm (centimeters); mm, (millimeters); μm (micrometers); nm (nanometers); bp (base pair); kDa or kD (kilodalton); cpm (counts per minute); ° C. (degrees Centigrade); ATCC (American Type Culture Collection, Manassas, Va.); Sigma (Sigma Aldrich, St. Louis, Mo.); Promega (Promega Corporation, Madison, Wis.); Qiagen (Qiagen, Chatsworth, Calif.); and Novagen (Novagen, Inc., Madison, Wis.).

Example 1

Detection of *B. burgdorferi* Toxin

In this Example, cultures of *B. burgdorferi* were grown and bioassays conducted in order to detect toxin produced by the organisms. In these experiments, the media in which the *B. burgdorferi* cultures were grown, as well as lysed organisms were observed for toxin activity.

Two assay systems were used in these experiments to measure ADP ribosyltransferase activity. One assay system detects the ribosylation of G-protein, while the other assay system detects the ribosylation of elongation factor 2 (EF2). The first assay system was the cholera toxin ADP-ribosyltransferase assay, which was conducted as known in the art and described by Murayama et al. (Murayama et al., *Biochem.*, 32:561–566 (1993)). The second assay system was likewise conducted as known in the art; this system was described by Chung and Collier (Chung, and Collier, *Infect. Immin.*, 16:832–841 (1977)). Ribosylation activity was detected in both assay systems, although at low levels. In the first assay system, cholera toxin (Sigma) was tested, as well as media conditioned by growth of *B. burgdorferi* cultures for 11 and 14 days. In the second assay system, IL2-DAB fusion toxin (positive control), PBS (negative control), and freeze-thaw lysed *B. burgdorferi* strain 2591 cultures (obtained from Dr. A. Barbour, University of Texas) were assayed for 15 minutes for ADP ribosyltransferase activity. Thirty second reactions were also carried out to demonstrate that the activity observed was enzymatic.

Figure 1B:
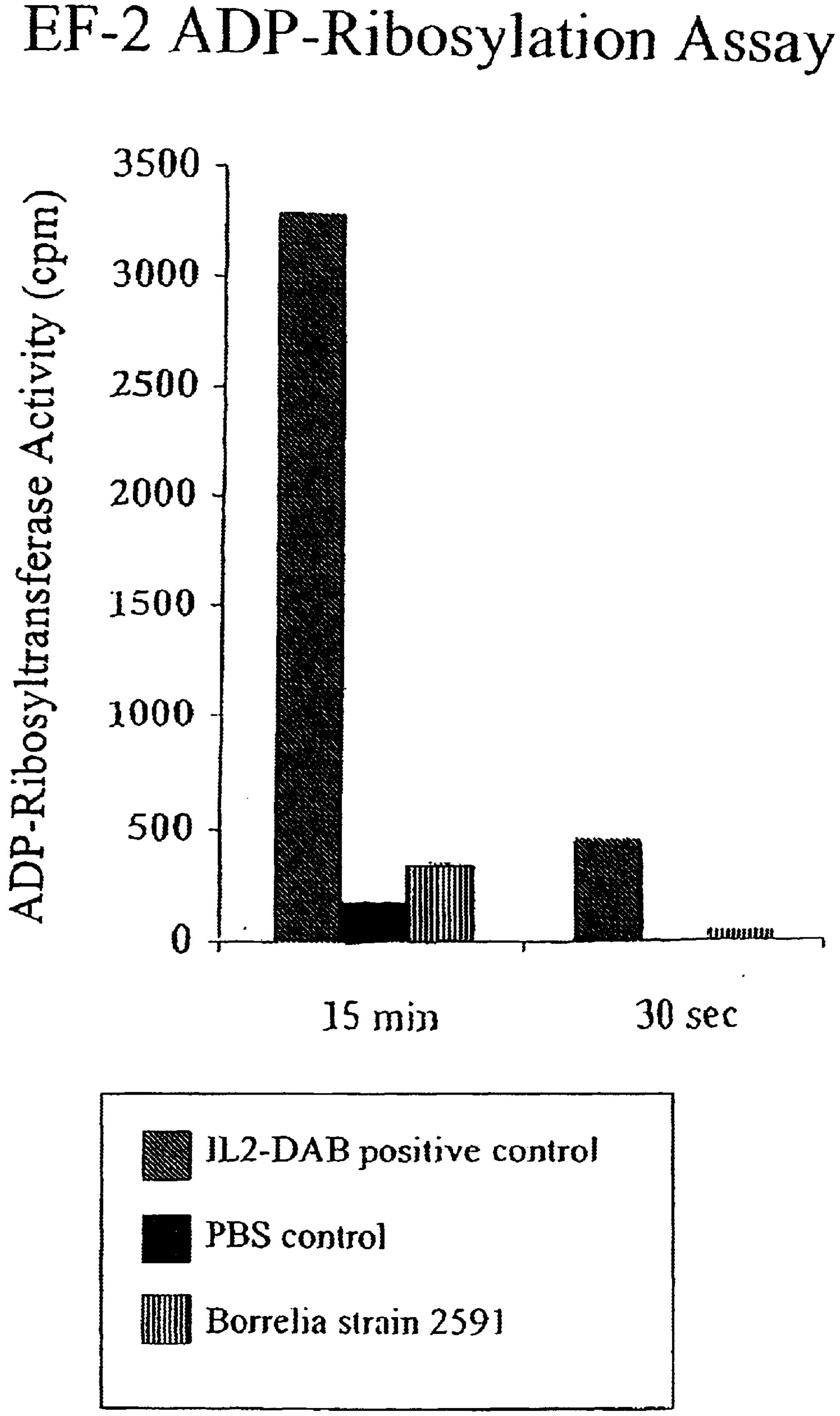

FIG. 1 provides a comparison of ADP-ribosyltransferase activity in these assay systems. The results in both Panel A and Panel B are shown corrected for background. Panel A shows the results of the agmatine ADP-ribosylation assay, using agmatine as a substrate. The assay results for 1 hour tests using, cholera toxin and media conditioned by growth of *B. burgdorferi* for 11 and 14 days are shown. Panel B shows the results with the diphtheria toxin system, using EF-2 as a substrate.

Example 2

Identification of *B. burgdorferi* Toxin Sequences

In this Example, experiments conducted to isolate and identify *B. burgdorferi* toxin(s) are described. First, PCR methods and degenerate primers were designed to hybridize regions of highly conserved amino acid sequences present in the catalytic domain active sites of known ADP-ribosylating toxins. The amino acid sequences based on sequences described by Alouf and Freer (eds.) (Alouf and Freer (eds.), *Sourcebook of Bacterial Protein Toxins*, Academic Press, San Diego, Calif. (Chapter 1) (1991)) are shown in Table 2 below. The ADP-ribosylating toxins were divided into two groups, with *E. coli*, Bordetella pertussis ("pertussis"), and Vibrio cholerae ("cholera") toxins in one group and Corynebacterium diphtheriae ("diphtheria") and Pseudomonas aeruginosa toxins in the second group, so that the primers would not be overly degenerate.

TABLE 2

Amino Acid Sequences of the Primers

| Organism | Region 1 | Region 2 |
|---|---|---|
| *V. cholerae* | N L Y D H A R G (SEQ ID NO: 7) | G H/Y S T Y Y I Y (SEQ ID NO: 8) |
| *E. coli* | N L Y D H A R G (SEQ ID NO: 9) | G H/Y S T Y Y I Y (SEQ ID NO: 10) |
| *B. pertussis* | N V L D H L T G (SEQ ID NO: 11) | G R F I G Y I Y (SEQ ID NO: 12) |
| *P. aeruginosa* | F V G Y H G T (SEQ ID NO: 13) | W R G F Y (SEQ ID NO: 14) |
| *C. diphtheriae* | F S S Y H G T (SEQ ID NO: 15) | W R K F Y (SEQ ID NO: 16) |

DNA sequences for degenerate "diphtheria/pseudomonas" oligonucleotides useful for amplification Bbtox1 from *B. burgdorferi* were derived from the amino acid sequences given in Table 1 above. Examples of useful primers shown in Table 3, below.

TABLE 3

Primer Sequences

| SEQUENCE | SEQUENCE IDENTIFICATION |
|---|---|
| 5'-GTN GGN TAC CAC GGN AC-3' | (SEQ ID NO: 19) |
| 5'-TCN TCN TAT CAT GGN AC-3' | (SEQ ID NO: 20) |
| 5'-AGN AGN TAC CAC GGN AC-3' | (SEQ ID NO: 21) |
| 5'-GTA GAA NCC NCG CCA-3' | (SEQ ID NO: 22) |
| 5'-ATA AAA NCC NTT CCA-3' | (SEQ ID NO: 23) |

To search for *B. burgdorferi* toxins, genomic DNA was extracted from *B. burgdorferi* strain 2591, for use as a PCR template. PCR was performed on this genomic material, using primers to each of the toxin groups described above. No PCR products were observed using the cholera/pertussis toxin primers. However, an amplification product of 600 bps was detected in the diphtherialPseudomonas toxin primer reaction. This 600 bp product was then cloned and sequenced. The DNA sequences were then compared with the published *B. burgdorferi* genome sequence (Fraser et al, *Nature* 390:5580–586 (1997)). The clone matched the DNA sequence of a hypothetical *B. burgdorferi* protein (BB0755) of unknown function in the Institute for Genomic Research (TIGR) database.

This BB0755 protein has also some homology to a *Treponema pallidum* polypeptide (SEQ ID NO:18) encoded by *Treponema pallidum* gene TP0819 (GenBank Acc. No. AE001252, SEQ ID NO:17). This treponemal protein has 55% homology at the amino acid level and 53% homology and nucleotide level with Bbtox1.

SEQ ID NOs:1 and 2 provide the nucleotide and peptide sequences of BB0755 from *B. burgdorferi* B31 (TIGR). SEQ ID NOs:3 and 4 provide the nucleotide and peptide sequences of Bbtox1 from *B. burgdorferi* strain 2591. There were four nucleotide differences detected between these two strains. Three of the nucleotide differences were identified as being at the third nucleotide of each codon and do not change the amino acid sequence of the peptide. The fourth difference is a Cytosine in strain B31 (879-gaaCatcca-888, SEQ ID NO:5), and a Thymine in strain 2591 (879-gaaTatcca-888, SEQ ED NO:6), causing a change in amino acid from Histidine to Tyrosine.

Next, the full-length coding region of BB0755 was cloned using methods known in the art. Primers to the 5' and 3' ends were synthesized and used to amplify the full-length BB0755. As indicated above, the nucleotide and peptide sequences for strain BB0755 are set forth in SEQ ID NOs:1 and 2, respectively. This sequence is located on the *B. burgdorferi* genome with the 5' end at 799016, and the 3' end at 798060. BamHI and HindlIl sites in the primers were then used to insert the amplified DNA into the linker site of a pET30a expression vector (Novagen). pET30a incorporated two epitope tags onto the N-terminus of *B. burgdorferi* toxin BB0755 (also referred to as "Bbtox1," and "Lymel"), namely a histidine tag (six histidine residues) for purification by metal chelation chromatography, and an S-protein tag (15 amino acids) for Western blot analysis. Expression of this construct is driven by a T7 lac promoter. In addition, a kanamycin resistance gene is encoded by the construct. The resulting expression plasmid construct is shown in FIG. 2. This expression plasmid construct is referred to as "pET30/Bbtox1" or "pET30//Lyme 1".

The expression plasmid construct was expressed, and the putative Bbtox1 was purified, using methods known in the art. At each stage of the induction and purification, samples were examined using methods known in the art. At each stage of the induction and purification, samples were examined using Western blots and an S-protein antibody. Following purification of the histidine tagged proteins by metal chelation chromatogaphy, a protein of the expected size of 37 kD was detected.

Example 3

Testing of Purified Bbtox1

In these experiments, purified recombinant Bbtox1 prepared as described in Example 2, above, was tested in ADP-ribosylation assays as described in Example 1. No activity was observed in the EF-2 ribosylation assay, indicating that Bbtox1 is not responsible for the low levels of activity observed in FIG. 1. This finding was surprising, as the primary sequence in Bbtox1 is conserved at the DNA level with diphtheriae toxin, but is out of frame with the amino acid sequence. Unexpectedly, ADP-ribosylation activity was detected in the agmatine ribosylation assay (i.e., which measures cholera toxin-like activity). Briefly, each sample was incubated in a substrate containing $^{14}$C-NAD and agmatine for 60 minutes at 30° C. The reactions were applied to an AGI-X2 columns and measured cpm. The activity of purified Bbtox1 is shown in comparison with lysed *B. burgdorferi* (not significantly different from background) and to native cholera toxin A subunit (CTA), An activity of approximately one-fifth that of the cholera toxin was detected. The results of this assay are shown in FIG. 3. In this Figure, the enzymatic activity is measured in cpm and corrected for background.

However, this assay does not distinguish whether Bbtox1 is intrinsically less active than cholera toxin or whether it has an endogenous target that is different from that of cholera toxin. In view of these results, the experiments described in Example 4, below were conducted.

Example 4

Activity of Bbtox1 in Cell Culture

ADP-ribosylation activity in the agmatine assay prompted us to examine Bbtox1 in a tissue culture model. Cholera toxin activity can be assessed using Y1 mouse adrenal cells (obtained from the ATCC, Manassas, Va.) (Donta et al., *Infect. Immun.*, 1993, 61:3282–3286). When Bbtox1 was added to Y1 cells, Bbtox1 caused a rounding of cells similar to that seen with cholera toxin. Y1 cells were treated with Tris buffer (control) or Bbtox1 (200 ng/ml). Morphologic changes in Y1 cells induced by Bbtox1 required 24 to 48 hours to be manifested. This time course is slower than that observed for cholera toxin on Y1 cells, i.e. 30 minutes to 2 hours. The morphologic changes elicited by Bbtox1 appear to be more similar to those of *C. difficile* toxin than that induced by cholera toxin. These findings suggest an alternate mechanism of action or a delay in uptake and trafficking of Bbtox1 to its cellular target.

We then tested the toxin in C6 rat glial cells. C6 cells were treated with Tris buffer (control) or Bbtox1 (200 ng/ml). Photographs were taken 18 hours post treatment C6 glial cells responded to Bbtox1 in a dose and time dependent manner (Table 4). Cells treated with 100 ng or 200 ng of Bbtox1 were at least 50% rounded by 8 hours. Both doses caused 100% rounding of cells by 36 hours post treatment. In contrast, cells treated with 20 ng of Bbtox1 required 5 days to achieve at least 50% rounding of cells. 2 ng/ml of Bbtox1 had no effect. These results indicate Bbtox1 is a time and dose dependent toxin.

TABLE 4

| Morphological effects of Bbtox in C6 glial cells | | | |
|---|---|---|---|
| | % Rounding of C6 Glial Cells | | |
| Treatment | 8 hours | 36 hours | 5 days |
| Bbtox1 200 ng | 58 | 100 | 100 |
| Bbtox1 100 ng | 51 | 100 | 100 |
| Bbtox1 20 ng | 32 | 25 | 57 |
| Control buffer | 27 | 10 | 22 |

C6 rat glial cells were plated at $1 \times 10^5$ per well 24 hours prior to treatment with Bbtox1. Control wells were treated with Bbtox1 Tris buffer. Morphological effects were measured as percentage of rounded cells per total cell number at 8 hours, 36 hours, and 5 days post treatment.

Bbtox1 induced cell death in both Yl and C6 cells as measured by trypan blue uptake (Table 5). When treated with Bbtox1 for 48 hours, both C6 and Y1 cells show increased cell death (30% and 35% respectively) in comparison with negative control wells (3%). The decrease in cell number of C6 cells and not Y1 cells at 48 hours post treatment probably reflects the difference in rate of toxin action between the two cell types.

TABLE 5

| Trypan blue evaluation of cell death in Y1 and C6 cells treated with Bbtox1 for 48 hours. | | | | |
|---|---|---|---|---|
| | C6 Glial Cells | | Y1 Adrenal Cells | |
| Treatment | Total Cell No. | % Cell Death | Total Cell No. | % Cell Death |
| Bbtox1 200 ng | $4.1 \times 10^5$ | 30 | $1.4 \times 10^6$ | 35 |
| Control buffer | $2.5 \times 10^6$ | 3 | $1.7 \times 10^6$ | 3 |

Cells were plated at $1 \times 10^5$ cells/well 24 hours prior to treatment with Bbtox1. Percent cell death was determined as cells stained with trypan blue per total cells counted.

The differences observed between C6 and Y1 cells may reflect differences in receptors, uptake, or trafficking of the toxin, for which experiments are proposed in specific aims. These 20 results suggest that Bbtox1 has an effect on the cytoskeleton (actin), perhaps by ADP-ribosylation of its target as seen with botulinum C3 exoenzyme that ADP-ribosylates the small GTPase Rho, inactivating it, and causing a disruption of the actin cytoskeleton (Chardin et al., 1989).

Brefeldin A (BFA), an inhibitor of the trans-golgi network, accelerated the onset of action of Bbtox1 on Y1 adrenal cells (Table 6). Bbtox1 without BFA exhibited fewer cells rounded at the same 24 hour time point. BFA treatment alone did not round cells (data not shown). The acceleration of onset of action by Brefeldin A implies a specific processing of the toxin to its target in the cell that is normally slowed down by passage through the Golgi. This data and the slow action of the toxin on cells in culture make it unlikely that Bbtox1 is a nonspecific protease.

TABLE 6

| Morphological effects (% rounding) of Bbtox1 in Y1 cells. | | |
|---|---|---|
| | % Rounding of Y1 Cells | |
| Treatment | 24 hours | 48 hours |
| Bbtox1 200 ng | 50 | 100 |
| Bbtox1 20 ng | 10 | 74 |
| Bbtox1 200 ng + BFA | 100 | 100 |
| Bbtox1 20 ng + BFA | 30 | 64 |
| Control Buffer | 10 | 10 |

Y1 mouse adrenal cells were plated at $1 \times 10^5$ per well 24 hours prior to treatment with Bbtox1 or Bbtox1 plus 0.5 kg Brefeldin A (BFA) at the indicated dosages. Percent rounding of total cells was determined at 24 and 48 hours post treatment.

Example 5

Tptox1 of *T. pallidum* and Syphilis

Full length Tptox 1 was amplified using primers to the 5' and 3' ends of the predicted protein sequence (TIGR). Treponema DNA for amplification was provided by Steve Norris at the University of Texas Houston. The sequence of the PCT product was confirmed to control for misincorporations. Using BamH1 and HindIII sites generated by the primers, the full length clone was inserted into the polylinker site of a pET30a expression vector (Novagen). We then expressed and partially purified the putative toxin Tptox1 (see general methods). To purify Tptox1, an inclusion body preparation of Tptox1 was passed over a His binding matrix. The purification of the expressed Tptox1 was examined by Western blot. A protein of the expected size of 37 kD was detected in the Western blot. Purified Tptox1 is believed to function as a toxin.

In summary, the present invention provides numerous advances and advantages over the prior art, including methods and compositions for the diagnosis, treatment, and prevention of Lyme disease. The present invention further provides numerous advances and advantages over the prior art, including methods and compositions for the diagnosis, treatment, and prevention of Syphilis.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in microbiology, molecular biology, immunology, and vaccine development, and/or related fields are intended to be within the scope of the present invention.

What is claimed is presented below and is followed by a Sequence Listing.

We claim:

1. An isolated peptide comprising SEQ ID NO:4.

2. An isolated peptide comprising at least 15 contiguous amino acids of SEQ ID NO:4.

3. The isolated peptide of claim 2, wherein said peptide comprises at least 20 contiguous amino acids.

4. The isolated peptide of claim 2, wherein said peptide comprises at least 30 contiguous amino acids.

5. An isolated peptide which has at least 75% sequence identity to SEQ ID NO:4.

6. The isolated peptide of claim 2, 3, or 4, which is recombinant.

7. A fusion peptide comprising a first non-toxic peptide linked to a second peptide comprising SEQ ID NO:4, wherein said first non-toxic peptide is a solubility enhancer, an affinity tag, or both.

8. A fusion peptide comprising a first non-toxic peptide linked to a second peptide which comprises at least 15 contiguous amino acids of SEQ ID NO:4, wherein said first non-toxic peptide is a solubility enhancer, an affinity tag, or both.

9. A fusion peptide comprising a first non-toxic peptide linked to a second peptide which has at least 75% sequence identity to SEQ ID NO:4, wherein said first non-toxic ptide is a solubility enhancer, an affinity tag, or both.

10. A composition comprising:

a peptide comprising SEQ ID NO:4, and a pharmaceutically acceptable carrier.

11. The composition of claim 10, wherein said SEQ ID NO:4 is present in an amount effective to produce antibodies.

12. A composition comprising:

a peptide which comprises at least 15 contiguous amino acids of SEQ ID NO:4;

a pharmaceutically acceptable carrier.

13. The composition of claim 12, wherein said peptide is comprised of at least 20 contiguous amino acids of SEQ ID NO. 4.

14. The composition of claim 12, wherein said peptide is comprised of at least 30 contiguous amino acids of SEQ ID NO:4.

15. The composition of claim 12, 13, or 14, wherein said peptide is present in an amount effective to produce antibodies to said peptide when administered to a subject.

16. The composition of claim 12, 13, or 14, wherein said peptide is present in an amount effective to produce antibodies for to said peptide when administered to a subject, and further comprising an adjuvant.

17. A composition comprising:

a peptide which has at least 75% sequence identity to SEQ ID NO:4; and a pharmaceutically acceptable carrier.

18. A composition comprising:

a fusion peptide comprising a first non-toxic peptide linked to a second peptide comprising SEQ ID NO:4, wherein said first non-toxic peptide is a solubility enhancer, an affinity tag, or both; and a pharmaceutically acceptable carrier.

19. composition of claim 18, wherein said fusion peptide is present in an amount effective to produce antibodies to said fusion peptide when administered to a subject.

20. A composition comprising:

a fusion peptide comprising a first non-toxic peptide linked to a second peptide which comprises at least 15 contiguous amino acids of SEQ ID NO:4, wherein said first non-toxic peptide is a solubility enhancer, an affinty, or both; and a pharmaceutically acceptable carrier.

21. The composition of claim 20, wherein said peptide is comprised of at least 20 contiguous amino acids of SEQ ID NO:4.

22. The composition of claim 20, wherein said peptide is comprised of at least 30 contiguous amino acids of SEQ ID NO:4.

23. The composition of claim 20, 21, or 22, wherein said fusion peptide is present in an amount effective to produce antibodies to said fusion peptide when administered to a subject.

24. The composition of claim 20, 21, or 22, wherein said fusion peptide is present in an amount effective to produce antibodies to said fusion peptide when administered to a subject, and further comprising an adjuvant.

25. A composition comprising:

a fusion peptide comprising a first non-toxic peptide linked to a second peptide comprising a peptide which has at least 75% sequence identity to SEQ ID NO:

a pharmaceutically acceptable carrier.

26. The composition of claim 25, wherein said fusion peptide is present in an amount effective to produce antibodies when administered to a subject.

27. The composition of claim 10, 11, 12, 13, 14, 17, 18, 19, 20, 21, 22, 25, or 26 further comprising an adjuvant.

* * * * *

SEQUENCE LISTING

<160> NUMBER OF SEQ ID NOS: 23

<210> SEQ ID NO 1
<211> LENGTH: 957
<212> TYPE: DNA
<213> ORGANISM: Borrelia burgdorferi

<400> SEQUENCE: 1

```
atgggattta atattaatat cataggaact ggaggaacaa ggccactcca caatagatat      60

ttgtcatccg tactaatcga atacgatgga gataactttt tgttcgattg tggtgaagga     120

acccaaatgt ctttaaggaa acaaaaaata tcctggcaaa aaataaaaat gatttgcatt     180

acacacttac atgctgacca catcacggga ctacttggaa tagtaatgct aatgtcacaa     240

agtggagaaa caagaaaaga accattaata atcgctggac ctgttggaat aaaaaactat     300

acacaagcta atataaatat gcttaaaata tataaaaact atgaaataat ttataaagaa     360

ataatcatag ataaaaccga aaaaataata tatgaagata aaacaaaaaa aattgaatac     420

actaaactaa aacattcaat agaatgtgtt ggatatttat ttatagaaaa agataaaccc     480

ggcaaattca acacagaaaa agcagaagag ctaaatattc ctaaagggcc tattagaaaa     540

gccctacaag atggaaaaga aatattggta aacggaaaaa ttataaagcc atcagaaata     600

cttggaaaat ctaaaaaagg actaaaagtt gcatacatta cagatactgg ttattttaaa     660

gaactcatac agcaaatcaa aaattttaac cttgtaataa ttgagagcac atttaaaaat     720

gagctaaaaa aagaagccga taaaaaactt cacttaacag ctggcggggc tgcaaatatt     780

gtcaagcaag caaaagtttt acaaacagga cttatccatt ttagtgaaag atatacatta     840

agaaaagatc ttgaaaactt actaaaggag gcaaaattgg aacatccaga cggagaaatt     900

tttttaacaa gagatggaat gaggcttgaa gcaaacaaaa ataactttat tattaaa        957
```

<210> SEQ ID NO 2
<211> LENGTH: 319
<212> TYPE: PRT
<213> ORGANISM: Borrelia burgdorferi

<400> SEQUENCE: 2

```
Met Gly Phe Asn Ile Asn Ile Ile Gly Thr Gly Gly Thr Arg Pro Leu
 1               5                  10                  15

His Asn Arg Tyr Leu Ser Ser Val Leu Ile Glu Tyr Asp Gly Asp Asn
            20                  25                  30

Phe Leu Phe Asp Cys Gly Glu Gly Thr Gln Met Ser Leu Arg Lys Gln
        35                  40                  45

Lys Ile Ser Trp Gln Lys Ile Lys Met Ile Cys Ile Thr His Leu His
    50                  55                  60

Ala Asp His Ile Thr Gly Leu Leu Gly Ile Val Met Leu Met Ser Gln
65                  70                  75                  80

Ser Gly Glu Thr Arg Lys Glu Pro Leu Ile Ile Ala Gly Pro Val Gly
                85                  90                  95

Ile Lys Asn Tyr Thr Gln Ala Asn Ile Asn Met Leu Lys Ile Tyr Lys
            100                 105                 110

Asn Tyr Glu Ile Ile Tyr Lys Glu Ile Ile Ile Asp Lys Thr Glu Lys
        115                 120                 125

Ile Ile Tyr Glu Asp Lys Thr Lys Lys Ile Glu Tyr Thr Lys Leu Lys
    130                 135                 140
```

-continued

```
His Ser Ile Glu Cys Val Gly Tyr Leu Phe Ile Glu Lys Asp Lys Pro
145                 150                 155                 160

Gly Lys Phe Asn Thr Glu Lys Ala Glu Glu Leu Asn Ile Pro Lys Gly
                165                 170                 175

Pro Ile Arg Lys Ala Leu Gln Asp Gly Lys Glu Ile Leu Val Asn Gly
            180                 185                 190

Lys Ile Ile Lys Pro Ser Glu Ile Leu Gly Lys Ser Lys Lys Gly Leu
        195                 200                 205

Lys Val Ala Tyr Ile Thr Asp Thr Gly Tyr Phe Lys Glu Leu Ile Gln
    210                 215                 220

Gln Ile Lys Asn Phe Asn Leu Val Ile Ile Glu Ser Thr Phe Lys Asn
225                 230                 235                 240

Glu Leu Lys Lys Glu Ala Asp Lys Lys Leu His Leu Thr Ala Gly Gly
                245                 250                 255

Ala Ala Asn Ile Val Lys Gln Ala Lys Val Leu Gln Thr Gly Leu Ile
            260                 265                 270

His Phe Ser Glu Arg Tyr Thr Leu Arg Lys Asp Leu Glu Asn Leu Leu
        275                 280                 285

Lys Glu Ala Lys Leu Glu His Pro Asp Gly Glu Ile Phe Leu Thr Arg
    290                 295                 300

Asp Gly Met Arg Leu Glu Ala Asn Lys Asn Asn Phe Ile Ile Lys
305                 310                 315
```

<210> SEQ ID NO 3
<211> LENGTH: 957
<212> TYPE: DNA
<213> ORGANISM: Borrelia burgdorferi

<400> SEQUENCE: 3

```
atgggattta atattaatat cataggaact ggaggaacaa ggccactcca caatagatat      60

ttgtcatccg tactaatcga atacgatgga gataactttt tattcgattg tggtgaagga     120

acccaaatgt ctttaaggaa acaaaaaata tcctggcaaa aaataaaaat gatttgcatt     180

acacacttac atgctgacca catcacggga ctacttggaa tagtaatgct aatgtcacaa     240

agtggagaaa caagaaaaga accattaata atcgctggac ctgttggaat aaaaaactat     300

acacaagcta atataaatat gcttaaaata tataaaaact atgaaataat ttataaagaa     360

ataatcatag ataaaaccga aaaaataata tatgaggata aaacaaaaaa aattgaatac     420

actaaactaa aacattcaat agaatgtgtt ggatatttat ttatagaaaa agataaaccc     480

ggcaaattca acacagaaaa agcagaagag ctaaatattc ctaaagggcc tattagaaaa     540

gccctacaag atggaaaaga aatattggta aacggaaaaa ttataaagcc atcagaaata     600

cttggaaaat ctaaaaaagg actaaaagtt gcatacatta cagatactgg ttattttaaa     660

gaactcatac agcaaatcaa aaattttaac cttgtaataa ttgagagcac atttaaaaac     720

gagctaaaaa aagaagccga taaaaaactt cacttaacag ctggcggggc tgcaaatatt     780

gtcaagcaag caaaagtttt acaaacagga cttatccatt ttagtgaaag atatacatta     840

agaaaagatc ttgaaaactt actaaaggag gcaaaattgg aatatccaga cggagaaatt     900

tttttaacaa gagatggaat gaggcttgaa gcaaacaaaa ataactttat tattaaa        957
```

<210> SEQ ID NO 4
<211> LENGTH: 319
<212> TYPE: PRT
<213> ORGANISM: Borrelia burgdorferi -continued

<400> SEQUENCE: 4

```
Met Gly Phe Asn Ile Asn Ile Ile Gly Thr Gly Gly Thr Arg Pro Leu
 1               5                  10                  15

His Asn Arg Tyr Leu Ser Ser Val Leu Ile Glu Tyr Asp Gly Asp Asn
            20                  25                  30

Phe Leu Phe Asp Cys Gly Glu Gly Thr Gln Met Ser Leu Arg Lys Gln
        35                  40                  45

Lys Ile Ser Trp Gln Lys Ile Lys Met Ile Cys Ile Thr His Leu His
    50                  55                  60

Ala Asp His Ile Thr Gly Leu Leu Gly Ile Val Met Leu Met Ser Gln
65                  70                  75                  80

Ser Gly Glu Thr Arg Lys Glu Pro Leu Ile Ile Ala Gly Pro Val Gly
                85                  90                  95

Ile Lys Asn Tyr Thr Gln Ala Asn Ile Asn Met Leu Lys Ile Tyr Lys
            100                 105                 110

Asn Tyr Glu Ile Ile Tyr Lys Glu Ile Ile Ile Asp Lys Thr Glu Lys
        115                 120                 125

Ile Ile Tyr Glu Asp Lys Thr Lys Lys Ile Glu Tyr Thr Lys Leu Lys
    130                 135                 140

His Ser Ile Glu Cys Val Gly Tyr Leu Phe Ile Glu Lys Asp Lys Pro
145                 150                 155                 160

Gly Lys Phe Asn Thr Glu Lys Ala Glu Glu Leu Asn Ile Pro Lys Gly
                165                 170                 175

Pro Ile Arg Lys Ala Leu Gln Asp Gly Lys Glu Ile Leu Val Asn Gly
            180                 185                 190

Lys Ile Ile Lys Pro Ser Glu Ile Leu Gly Lys Ser Lys Lys Gly Leu
        195                 200                 205

Lys Val Ala Tyr Ile Thr Asp Thr Gly Tyr Phe Lys Glu Leu Ile Gln
    210                 215                 220

Gln Ile Lys Asn Phe Asn Leu Val Ile Ile Glu Ser Thr Phe Lys Asn
225                 230                 235                 240

Glu Leu Lys Lys Glu Ala Asp Lys Lys Leu His Leu Thr Ala Gly Gly
                245                 250                 255

Ala Ala Asn Ile Val Lys Gln Ala Lys Val Leu Gln Thr Gly Leu Ile
            260                 265                 270

His Phe Ser Glu Arg Tyr Thr Leu Arg Lys Asp Leu Glu Asn Leu Leu
        275                 280                 285

Lys Glu Ala Lys Leu Glu Tyr Pro Asp Gly Glu Ile Phe Leu Thr Arg
    290                 295                 300

Asp Gly Met Arg Leu Glu Ala Asn Lys Asn Asn Phe Ile Ile Lys
305                 310                 315
```

<210> SEQ ID NO 5
<211> LENGTH: 9
<212> TYPE: DNA
<213> ORGANISM: Borrelia burgdorferi

<400> SEQUENCE: 5 gaacatcca 9

<210> SEQ ID NO 6
<211> LENGTH: 9
<212> TYPE: DNA
<213> ORGANISM: Borrelia burgdorferi

<400> SEQUENCE: 6

-continued gaatatcca 9

<210> SEQ ID NO 7
<211> LENGTH: 8
<212> TYPE: PRT
<213> ORGANISM: V. cholerae

<400> SEQUENCE: 7

Asn Leu Tyr Asp His Ala Arg Gly
1 5

<210> SEQ ID NO 8
<211> LENGTH: 8
<212> TYPE: PRT
<213> ORGANISM: V. cholerae
<220> FEATURE:
<221> NAME/KEY: VARIANT
<222> LOCATION: (2)...(2)
<223> OTHER INFORMATION: His or Tyr

<400> SEQUENCE: 8

Gly Xaa Ser Thr Tyr Tyr Ile Tyr
1 5

<210> SEQ ID NO 9
<211> LENGTH: 8
<212> TYPE: PRT
<213> ORGANISM: E. coli

<400> SEQUENCE: 9

Asn Leu Tyr Asp His Ala Arg Gly
1 5

<210> SEQ ID NO 10
<211> LENGTH: 8
<212> TYPE: PRT
<213> ORGANISM: E. coli
<220> FEATURE:
<221> NAME/KEY: VARIANT
<222> LOCATION: (2)...(2)
<223> OTHER INFORMATION: His or Tyr

<400> SEQUENCE: 10

Gly Xaa Ser Thr Tyr Tyr Ile Tyr
1 5

<210> SEQ ID NO 11
<211> LENGTH: 8
<212> TYPE: PRT
<213> ORGANISM: B. pertussis

<400> SEQUENCE: 11

Asn Val Leu Asp His Leu Thr Gly
1 5

<210> SEQ ID NO 12
<211> LENGTH: 8
<212> TYPE: PRT
<213> ORGANISM: B. pertussis

<400> SEQUENCE: 12

Gly His Phe Ile Gly Tyr Ile Tyr
1 5

<210> SEQ ID NO 13

-continued

<211> LENGTH: 7
<212> TYPE: PRT
<213> ORGANISM: P. aeruginosa

<400> SEQUENCE: 13

Phe Val Gly Tyr His Gly Thr
1 5

<210> SEQ ID NO 14
<211> LENGTH: 5
<212> TYPE: PRT
<213> ORGANISM: P. aeruginosa

<400> SEQUENCE: 14

Trp Arg Gly Phe Tyr
1 5

<210> SEQ ID NO 15
<211> LENGTH: 7
<212> TYPE: PRT
<213> ORGANISM: C. diphtheriae

<400> SEQUENCE: 15

Phe Ser Ser Tyr His Gly Thr
1 5

<210> SEQ ID NO 16
<211> LENGTH: 5
<212> TYPE: PRT
<213> ORGANISM: C. diphtheriae

<400> SEQUENCE: 16

Trp Arg Lys Phe Tyr
1 5

<210> SEQ ID NO 17
<211> LENGTH: 762
<212> TYPE: DNA
<213> ORGANISM: Treponemal pallidum

<400> SEQUENCE: 17
atgagcctgt gtctcggtca tattttttcc cgctctcgtt ctcccctcac ccccgagcgt 60
agggagtctc tccggcgcct gcaagagacg ctcggcgtta aattccgcga tcctaccgca 120
ctcgaccagg cactttctca ccggtctttg ttttcctcaa aagaggacca ttgcggtgtg 180
cgccacaatg agcgcatgga gtttctcggg gatgccgtgc ttggcgcggt agccgccgct 240
tgcctgtatc gcgcacttcc cgacagtcac gagggggatt tagcaaagac taaggcggtg 300
ctcgtgtcta ctgacaccct ctcggacatt gccttgagcc tgcgtataga ccactacctt 360
ctgctaggaa aggggagga gctttcagga ggtcggcaca aaaaagccat ccttgccgac 420
gctaccgaag ctgtcatcgg tgcgcttttt ttggattcag ggttcaaggc ggcagagcgt 480
tttgttctcc gtctcctgct cccccgtgtc cgccccatac gagagaaaaa tttgcaccat 540
gactacaaat ctaccctcca ggtgcttgca catcagcgct atcgtagtaa gccggagtac 600
acggtcgtca agcgcaccgg acctgatcac agcgtacgct tctgggtgga tgttaccgtt 660
ggcgatgcac gcttcggacc cggttatggc accagcaaaa aaagcgcaga acagtgcgcc 720
gctcgccttg catgggaaca attatccggc accctccggg ag 762

<210> SEQ ID NO 18
<211> LENGTH: 254

-continued

<212> TYPE: PRT
<213> ORGANISM: Treponemal pallidum

<400> SEQUENCE: 18

```
Met Ser Leu Cys Leu Gly His Ile Phe Ser Arg Ser Arg Ser Pro Leu
 1               5                  10                  15

Thr Pro Glu Arg Arg Glu Ser Leu Arg Arg Leu Gln Glu Thr Leu Gly
            20                  25                  30

Val Lys Phe Arg Asp Pro Thr Ala Leu Asp Gln Ala Leu Ser His Arg
        35                  40                  45

Ser Leu Phe Ser Ser Lys Glu Asp His Cys Gly Val Arg His Asn Glu
    50                  55                  60

Arg Met Glu Phe Leu Gly Asp Ala Val Leu Gly Ala Val Ala Ala Ala
65                  70                  75                  80

Cys Leu Tyr Arg Ala Leu Pro Asp Ser His Glu Gly Asp Leu Ala Lys
                85                  90                  95

Thr Lys Ala Val Leu Val Ser Thr Asp Thr Leu Ser Asp Ile Ala Leu
            100                 105                 110

Ser Leu Arg Ile Asp His Tyr Leu Leu Leu Gly Lys Gly Glu Glu Leu
        115                 120                 125

Ser Gly Gly Arg His Lys Lys Ala Ile Leu Ala Asp Ala Thr Glu Ala
    130                 135                 140

Val Ile Gly Ala Leu Phe Leu Asp Ser Gly Phe Lys Ala Ala Glu Arg
145                 150                 155                 160

Phe Val Leu Arg Leu Leu Leu Pro Arg Val Arg Pro Ile Arg Glu Lys
                165                 170                 175

Asn Leu His His Asp Tyr Lys Ser Thr Leu Gln Val Leu Ala His Gln
            180                 185                 190

Arg Tyr Arg Ser Lys Pro Glu Tyr Thr Val Val Lys Arg Thr Gly Pro
        195                 200                 205

Asp His Ser Val Arg Phe Trp Val Asp Val Thr Val Gly Asp Ala Arg
    210                 215                 220

Phe Gly Pro Gly Tyr Gly Thr Ser Lys Lys Ser Ala Glu Gln Cys Ala
225                 230                 235                 240

Ala Arg Leu Ala Trp Glu Gln Leu Ser Gly Thr Leu Arg Glu
                245                 250
```

<210> SEQ ID NO 19
<211> LENGTH: 17
<212> TYPE: DNA
<213> ORGANISM: Artificial Sequence
<220> FEATURE:
<223> OTHER INFORMATION: Borrelia burgdorferi degenerate primer
<221> NAME/KEY: variation
<222> LOCATION: (3)...(3)
<223> OTHER INFORMATION: A or C or T/U or G or Other
<221> NAME/KEY: variation
<222> LOCATION: (6)...(6)
<223> OTHER INFORMATION: A or C or T/U or G or Other
<221> NAME/KEY: variation
<222> LOCATION: (15)...(15)
<223> OTHER INFORMATION: A or C or T/U or G or Other

<400> SEQUENCE: 19
gtnggntacc acggnac 17

<210> SEQ ID NO 20
<211> LENGTH: 17
<212> TYPE: DNA
<213> ORGANISM: Artificial Sequence -continued

```
<220> FEATURE:
<223> OTHER INFORMATION: Borrelia burgdorferi degenerate primer
<221> NAME/KEY: variation
<222> LOCATION: (3)...(3)
<223> OTHER INFORMATION: A or C or T/U or G or Other
<221> NAME/KEY: variation
<222> LOCATION: (6)...(6)
<223> OTHER INFORMATION: A or C or T/U or G or Other
<221> NAME/KEY: variation
<222> LOCATION: (15)...(15)
<223> OTHER INFORMATION: A or C or T/U or G or Other

<400> SEQUENCE: 20

tcntcntatc atggnac                                              17


<210> SEQ ID NO 21
<211> LENGTH: 17
<212> TYPE: DNA
<213> ORGANISM: Artificial Sequence
<220> FEATURE:
<223> OTHER INFORMATION: Borrelia burgdorferi degenerate primer
<221> NAME/KEY: variation
<222> LOCATION: (3)...(3)
<223> OTHER INFORMATION: A or C or T/U or G or Other
<221> NAME/KEY: variation
<222> LOCATION: (6)...(6)
<223> OTHER INFORMATION: A or C or T/U or G or Other
<221> NAME/KEY: variation
<222> LOCATION: (15)...(15)
<223> OTHER INFORMATION: A or C or T/U or G or Other

<400> SEQUENCE: 21

agnagntacc acggnac                                              17


<210> SEQ ID NO 22
<211> LENGTH: 15
<212> TYPE: DNA
<213> ORGANISM: Artificial Sequence
<220> FEATURE:
<223> OTHER INFORMATION: Borrelia burgdorferi degenerate primer
<221> NAME/KEY: variation
<222> LOCATION: (7)...(7)
<223> OTHER INFORMATION: A or C or T/U or G or Other
<221> NAME/KEY: variation
<222> LOCATION: (10)...(10)
<223> OTHER INFORMATION: A or C or T/U or G or Other

<400> SEQUENCE: 22

gtagaanccn cgcca                                                15


<210> SEQ ID NO 23
<211> LENGTH: 15
<212> TYPE: DNA
<213> ORGANISM: Artificial Sequence
<220> FEATURE:
<223> OTHER INFORMATION: Borrelia burgdorferi degenerate primer
<221> NAME/KEY: variation
<222> LOCATION: (7)...(7)
<223> OTHER INFORMATION: A or C or T/U or G or Other
<221> NAME/KEY: variation
<222> LOCATION: (10)...(10)
<223> OTHER INFORMATION: A or C or T/U or G or Other

<400> SEQUENCE: 23

ataaaanccn ttcca                                                15
```